United States Patent [19]
Heino et al.

[11] Patent Number: 6,096,707
[45] Date of Patent: Aug. 1, 2000

[54] INTEGRIN BINDING PEPTIDE AND USE THEREOF

[75] Inventors: Jyrki Heino, Turlu; Johanna Ivaska; Jarmo Käpylä, both of Turku, all of Finland

[73] Assignee: BioTie Therapies Ltd., Turku, Finland

[21] Appl. No.: 08/893,526

[22] Filed: Jul. 11, 1997

[51] Int. Cl.[7] .............................. A61K 38/12; C07K 5/12
[52] U.S. Cl. ................................ 514/12; 514/13; 514/14; 514/15; 514/16; 514/17; 514/18; 530/317; 530/324; 530/325; 530/326; 530/327; 530/328; 530/329; 530/330; 530/331
[58] Field of Search ................................... 530/324–331; 514/12–18

[56] References Cited

U.S. PATENT DOCUMENTS

| | | | |
|---|---|---|---|
| 5,179,007 | 1/1993 | Jarvis et al. | 435/68.1 |
| 5,627,263 | 5/1997 | Ruoslahti et al. | 530/327 |

OTHER PUBLICATIONS

Bergelson, J.M. et al., "The Integrin VLA–2 Binds Echovirus 1 and Extracellular Matrix Ligands by Different Mechanisms," *J. Clin. Invest.* 92(1):232–239 (Jul., 1993).

Busk, M. et al., "Characterization of the Integrin $\alpha v\beta 6$ as a Fibronectin–binding Protein," *J. Biol. Chem.* 267(9):5790–5796 (Mar., 1992).

Cardarelli, P.M. et al., "The Collagen Receptor $\alpha 2\beta 1$, from MG–63 and HT1080 Cells, Interacts with a Cyclic RGD Peptide," *J. Biol. Chem.* 267(32):23159–23164 (Nov., 1992).

De Luca, M. et al., "Jararhagin and Jaracetin: Novel Snake Venom Inhibitors of the Integrin Collagen Receptor, $\alpha_2\beta_1$," *Biochem. Biophys. Res. Comm.* 206(2):570–576 (Jan., 1995).

Drake, S.L. et al., "Structural Features of Fibronectin Synthetic Peptide FN–C/H II, Responsible for Cell Adhesion, Neurite Extension, and Heparan Sulfate Binding," *J. Biol. Chem.* 268(21):15859–15867 (Jul., 1993).

Eble, J.A. et al., "The $\alpha 1\beta 1$ integrin recognition site of the basement membrane collagen molecule $[\alpha 1(IV)]_2\beta 2(IV)$," *EMBO J.* 12(12):4795–4802 (Dec., 1993).

Elices, M.J. et al., "Receptor Functions for the Integrin VLA–3: Fibronectin, Collagen, and Laminin Binding Are Differentially Influenced by ARG–GLY–ASP Peptide and by Divalent Cations," *J. Cell. Biol.* 112(1):169–181 (Jan., 1991).

Emini, E.A. et al., "Induction of Hepatitis A Virus–Neutralizing Antibody by a Virus–Specific Synthetic Peptide," *J. Virol.* 55(3):836–839 (Sep., 1985).

Gullberg, D. et al., "Analysis of $\alpha_1\beta_1$, and $\alpha_3\beta_1$ integrins in cell–collagen interactions: identification of conformation dependent $\alpha_1\beta_1$ binding sites in collagen type I," *EMBO J.* 11(11):3865–3873 (Nov., 1992).

Hemler, M.E., "VLA Proteins in the Integrin Family: Structures, Functions, and Their Role on Leukocytes," *Annu. Rev. Immunol.* 8:365–400 (1990).

Hynes, R.O., "Intergrins: Versatility, Modulation, and Signaling in Cell Adhesion," *Cell* 69:11–25 (Apr., 1992).

Kamata, T. et al., "Identification of Putative Ligand Binding Sites within I Domain of Integrin $\alpha 2\beta 1$ (VLA–2, CD49b/CD29)," *J. Biol. Chem.* 269(13):9659–9663 (Apr., 1994).

Kamata, T. and Y. Takada, "Direct Binding of Collagen to the I Domain of Integrin $\alpha 2\beta 1$ (VLA–2, CD49b/CD29) in a Divalent Cation–independent Manner," *J. Biol. Chem.* 269(42):26006–26010 (Oct., 1994).

Kern, A. et al., "The Role of the I Domain in Ligand Binding of the Human Integrin $\alpha_1\beta_1$," *J. Biol. Chem.* 269(36):22811–22816 (Sep., 1994).

Koivunen, E. et al., "Selection of Peptides Binding to the $\alpha_5\beta_1$ Integrin from Phage Display Library," *J. Biol. Chem* 268(27):20205–20210 (Sep., 1993).

Kyte, J. and R.F. Doolittle, "A Simple Method for Displaying the Hydropathic Character of a Protein," *J. Mol. Biol.* 157:105–132 (May, 1982).

Michishita, M. et al., "A Novel Divalent Cation–Binding Site in the A Domain of the $\beta 2$ Integrin CR3 (CD11b/CD18) Is Essential for Ligand Binding," *Cell* 72:857–867 (Mar., 1993).

Paine, M.J.I. et al., "Purification, Cloning, and Molecular Characterization of a High Molecular Weight Hemorrhagic Metalloprotease, Jararhagin, form *Bothrops jararaca* Venom," *J. Biol. Chem.* 267(32):22869–22876 (Nov., 1992).

Pfaff, M. et al., "Integrin and Arg–Gly–Asp Dependence of Cell Adhesion to the Native and Unfolded Triple Helix of Collagen Type VI," *Exp. Cell Res.* 206:167–176 (May, 1993).

Ruoslahti, E., "Integrins," *J. Clin. Invest.* 87:1–5 (Jan., 1991).

Shih, D.–T. et al., "Structure/Function Analysis of the Integrin $\beta 1$ Subunit by Epitope Mapping," *J. Cell. Biol.* 122(6):1361–1371 (Sep., 1993).

Staatz, W.D. et al., "Identification of a Tetrapeptide Recognition Sequence for the $\alpha_2\beta_1$ Integrin in Collagen," *J. Biol. Chem.* 266(12):7363–7367 (Apr., 1991).

Takada, Y. and M.E. Helmer, "The Primary Structure of the VLA–2/Collagen Receptor $\alpha^2$ Subunit (Platelet GPIa): Homology to Other Integrins and the Presence of a Possible Collagen–binding Domain," *J. Cell Biol.* 109:397–407 (Jul., 1989).

Tuckwell, D. et al., "Integrins $\alpha 2$ I–domain is a binding site for collagens," *J. Cell Sci.* 108: 1629–1637 (Apr., 1995).

Vihinen, P. et al., "Integrin $\alpha 2\beta 1$ in Tumorigenic Human Osteosarcoma Cell Lines Regulates Cell Adhesion, Migration, and Invasion by Interaction with Type I Collagen," *Cell Growth & Differentiation* 7(4):439–447 (Apr., 1996).

Vogel, B.E. et al., "A Novel Integrin Specificity Exemplified by Binding of the $\alpha_v\beta_5$ Integrin to the Basic Domain of the HIV Tat Protein and Vitronectin," *J. Cell. Biol.* 121(2):461–468 (Apr., 1993).

*Primary Examiner*—Julie Burke
*Attorney, Agent, or Firm*—Sterne, Kessler, Goldstein & Fox P.L.L.C.

[57] ABSTRACT

Cyclic peptides comprising three colinear amino acids, arginine-lysine-lysine (RKK) are provided that bind to the integrin $\alpha 2I$ domain and are potent inhibitors of its interaction with collagens I and IV and laminin-1. Methods of using such peptides to block integrin function and to inhibit cell migration are also provided.

40 Claims, 13 Drawing Sheets

INTEGRIN BINDING PEPTIDE AND USE THEREOF

FIELD OF THE INVENTION

The invention is in the field of protein therapeutics. Specifically, the invention is directed to cyclic peptides and the uses thereof, especially the use of these peptides to block or inhibit the biological activity of integrin.

BACKGROUND OF THE INVENTION

Integrins are heterodimeric cell surface glycoproteins that are composed of non-covalently associated $\alpha$ and $\beta$ subunits. Sixteen $\alpha$ subunits and eight $\beta$ subunits have been identified. Over 20 different combinations of these subunits have been found.

Integrins anchor cells to their surroundings by mediating cell-matrix and cell—cell interactions (for review, see Hemler, M. E. *Annu. Rev. Immunol.* 8:365–400 (1990); and Hynes, R. O. *Cell* 69:11–25 (1992) and citations therein). Recognition of the arginine-glycine-aspartic acid (RGD) sequence in extracellular matrix proteins by the integrins is a fundamental phenomenon in cell-matrix interaction. Fibronectin is the prototype of a RGD-containing protein. In addition, a large number of other matrix molecules in mammals, birds, frogs, and insects mediate cell adhesion via their RGD-sequence. Integrin heterodimers containing a $\beta 1$, $\beta 3$, $\beta 5$, or $\beta 6$ subunit can form RGD-dependent receptors (Ruoslahti, E., *J. Clin. Invest.* 87:1–5 (1991); Busk, M. et al., *J. Biol. Chem.* 267:7875–7881 (1992); and Elices, M. J. et al., *J. Cell Biol.* 112:169–181 (1991)). In the $\beta 1$ subunit the RGD-binding site has been mapped to the amino terminal half of the molecule and there is some evidence suggestive of the possibility that the $\alpha$ subunit may influence this interaction (Shih, D. T. et al., *J. Cell Biol.* 122:1361–1371 (1993)). All together, ten integrin heterodimers share the common $\beta 1$ subunit, and therefore have also the putative RGD-binding site. Most of the $\beta 1$ integrins have, however, additional mechanisms for ligand binding. Denatured fibrillar collagens are recognized by the RGD-dependent integrins, like $\alpha 5\beta 1$, whereas native collagens interact with integrins in a RGD-independent manner (Gullberg, D. et al., *EMBO J.* 11:3865–3873 (1992)).

Two integrins, the $\alpha 1\beta 1$ and $\alpha 2\beta 1$ heterodimers, are the major cellular receptors for native collagens and like all integrins their interaction with ligands is dependent on divalent cations (Staatz, W. D. et al., *J. Biol. Chem.* 266:7363–7387 (1991)). Integrin $\alpha 2\beta 1$ is expressed for example on epithelial cells, platelets, granulation tissue cells, and various cancer cells. Biological phenomena in which $\alpha 2\beta 1$ integrin activity (function) is essential include collagen-induced platelet aggregation, cell migration on collagen, and cell-dependent reorganization of collagen fibers. In cancer biology, the $\alpha 2\beta 1$ integrin has been associated with an invasive cell phenotype and it can be a marker for aggressive melanoma. On the other hand, overexpression of $\alpha 2\beta 1$ integrin in breast cancer cells restores the normal phenotype. Like other integrins, $\alpha 2\beta 1$ can also generate signals regulating cellular functions and gene expression. Especially, the MRNA levels of collagenase-1 seem to be controlled by $\alpha 2\beta 1$ integrin.

The $\alpha 1$ and $\alpha 2$ subunits differ in their structure from all other $\beta 1$ associated $\alpha$ subunits in the sense that they contain a special "inserted" domain, the I domain, which resembles the A domain found e.g. in von Willenbrand factor (Michishita, M. et al., *Cell* 72:857–867 (1993)). It is evident that $\alpha 1$I and $\alpha 2$I domains are responsible for the primary recognition of collagen by the corresponding integrins (Kamata, T. et al., *J. Biol. Chem.* 269:9659–9663 (1994); Kamata, T. et al., *J. Biol. Chem.* 269:26006–26101 (1994); Kern, A. et al., *J. Biol. Chem.* 269:22811–22816 (1994)). Two other ligands for $\alpha 2\beta 1$ integrin, namely lamin-1 and echovirus-1, both bind to the $\alpha 2$I-domain, as well. However, echovirus-1 seems to recognize a different site in $\alpha 2$I domain than the matrix proteins (Bergelson, J. M. et al., *J. Clin. Invest.* 92:232–239 (1993)).

The binding sites of $\alpha 1\beta 1$ and $\alpha 2\beta 1$ integrins in collagens have been localized in the triple-helical areas of the molecules (Eble, J. A. et al., *EMBO J.* 12:4795–4802 (1993); Gulberg, D. et al., *EMBO J.* 11:3865–3873 (1992)). One peptide sequence derived from the collagen a chain has been reported to block integrin-collagen interaction, but in many studies it has been ineffective and it probably does not represent the actual binding site in collagen (Cardarelli, P. M. et al., *J. Biol. Chem.* 267:23159–23164 (1992); Pfaff, M. et al., *Exp. Cell Res.* 206:167–176 (1993); and Tuckwell, D. et al., *J. Cell Sci.* 108:1629–1637 (1995)). More likely collagen-receptor integrins recognize amino acid residues from more than one collagen $\alpha$ chain. In type IV collagen-$\alpha 1\beta 1$ integrin interaction, the importance of one arginine and two aspartic acid residues, all from different $\alpha$ chains of the collagen, has been indicated (Eble, J. A. et al., *EMBO J.* 12:4795–4802 (1993)).

The known matrix molecule ligands for $\alpha 2\beta 1$ integrin do not contain an RKK(H) sequence. An arginine-rich linear peptide comprising an RKK sequence, derived from a human immunodeficiency virus Tat protein has been shown to interact with $\alpha V\beta 5$ integrin (Vogel, B. E. et al., *J. Cell Biol.* 121:461–468 (1993)). However the integrin-peptide interaction was found to be stable in the presence of EDTA, indicating a distinct binding mechanism. There is also a previously described heparin sulfate binding sequence in fibronectin containing an RKK sequence motif, which, however, obviously is non-functional in terms of the integrin r$\alpha 2$I domain binding (Drake et al., *J. Biol. Chem.* 268:15859–15867 (1993)).

The venom from several snake species contains disintegrin-like proteins, which block platelet integrin function and are responsible for the anticoagulation effect of the venoms. These proteins have helped to understand the molecular mechanisms of integrin function and they have potential value also in the development of new drugs. Many of the disintegrins have an RGD-sequence and they inhibit the function of platelet $\alpha IIb\beta 3$ and $\alpha V\beta 3$ integrins. In jararhagin, a disintegrini/metalloproteinase from pit viper *Bothrops jararaca*, the sequence ECD replaces RGD (Paine, M. J. I. et al., *J. Biol. Chem.* 267:22869–22876 (1992)). Jararhagin is a potent inhibitor of collagen-induced platelet aggregation and its effect is based on the inhibition of $\alpha 2\beta 1$ integrin function (De Luca, M. et al., *Biochem. Biophys. Res. Commun.* 206:570–576 (1995)). The exact mechanism of its action has been unknown. Integrin $\alpha 2\beta 1$ may also interact with jaracetin, a snake venom protein containing the disintegrin domain of jararhagin, but the interaction seems to be weaker than with jararhagin (De Luca, M. et al., *Biochem. Biophys. Res. Commun.* 206:570–576 (1995)).

SUMMARY OF THE INVENTION

The present invention provides cyclic peptides that bind to the human $\alpha 2$I domain (native and recombinant). In addition, they are potent inhibitors of human integrin interaction with collagens I and IV and laminin-1.

The cyclic peptides of the invention were originally derived from the metalloproteinase domain of jararhagin.

Each of the novel integrin binding proteins of the invention comprises a colinear sequence of three amino acids, arginine-lysine-lysine (RKK). The presence of the RKK sequence in the cyclic form imparts integrin binding activity.

The invention further provides cyclic peptides that contain one or more copies of the RKK sequence motif within the sequence of the peptide, such copies being sufficient to provide the peptide with the ability to decrease the interaction of integrin with collagen.

The invention further provides cyclic peptides that comprise the amino acid sequence $X_1RKKX_2X_3X_4X_5X_6$ (SEQ ID No. 1) wherein amino acids $X_1-X_6$ are any amino acid but preferably $X_2$ is histidine (H).

The invention further provides cyclic peptides that preferably comprise the amino acid sequence $X_1RKKX_2X_3X_4X_5$, (SEQ ID No. 2) wherein amino acids $X_1-X_5$ are any amino acid but preferably $X_2$ is histidine (H).

The invention further provides cyclic peptides that more preferably comprise an amino acid sequence $X_1RKKX_2X_3X_4$, (SEQ ID No. 3) wherein amino acids $X_1-X_4$ are any amino acids but preferably $X_2$ is histidine.

The invention further provides two cyclic peptides, CTRKKHDNC (SEQ ID NO: 4) and CTRKKHDNAQC (SEQ ID NO: 5), containing amino acids 241–247 (CTRKKHD; SEQ ID No. 6) and 241–249 (CTRKKHDNA; SEQ ID No. 7), respectively, of the metalloproteinase domain of jararhagin, and cyclic fragments of these peptides that lack one or more amino acids, especially one or more of an amino acid selected from the group consisting of C, T, H, D, N, A and/or Q.

The present invention further provides methods for using these peptides to block integrin function, and to treat patients having a physiological condition or disease in need of such blocking activity.

The cyclic integrin binding peptides according to the present invention are also useful for isolating α2-containing integrins from a sample mixture.

DETAILED DESCRIPTION OF THE PREFERRED EMBODIMENTS

Figure 1A:
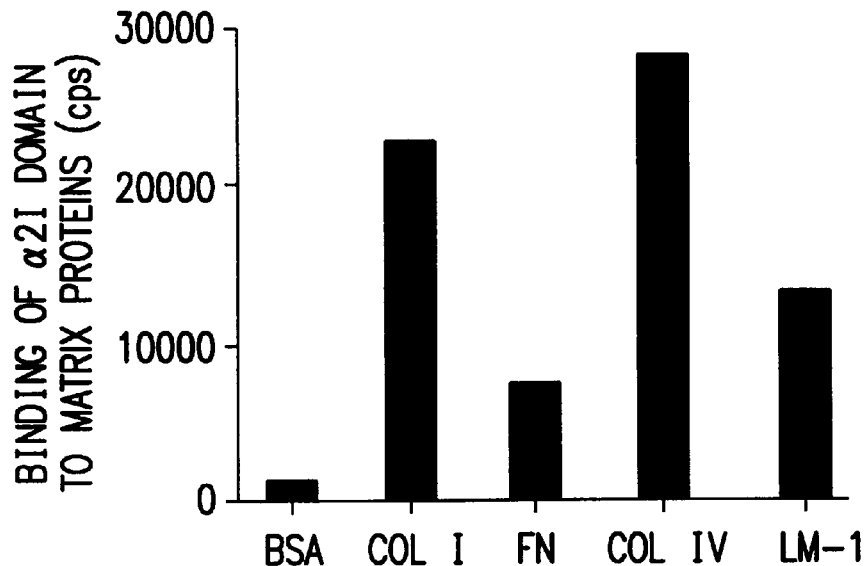
FIGS. 1(A–D). Binding of europium labeled rα2I to different substrates in a solid phase assay. Microtiter plate wells were precoated with type I collagen, type IV collagen, laminin-1, and fibronectin. rα2I was allowed to attach for 3 h (A). rα2I was allowed to attach to type I collagen in the presence of EDTA (B) or $MgCl_2$ and various concentrations of *Bothrops jararaca* venom (C). Alternatively wells were precoated with *Bothrops jararaca* venom and rα2I was allowed to attach for 3 h in the presence of $MgCl_2$ (D).

In the description that follows, a number of terms used in the medical and protein arts are extensively utilized. In order to provide a clear and consistent understanding of the specification and claims, including the scope to be given such terms, the following definitions are provided.

By a "patient" is meant an animal or human subject in need of veterinary or medical treatment, especially in need of treatment with a composition of the invention.

By "treatment" or "treating" is meant the administration of an efficacious amount of a composition containing one or more of the peptides described herein to a patient in need of the same, for purposes that may include prophylaxis, amelioration, prevention or cure of a disorder or potential disorder susceptible to such agents.

By "administration" is meant the introduction of a desired substance into a patient by any appropriate method. Useful methods of administration include, but are not limited to, parenteral (e.g., intravenous), intramuscular, subdermal, iontophoretic, oral, rectal, and enteral administration.

By an "efficacious amount" is meant an amount sufficient to achieve the stated desired end. An efficacious amount of a peptide of the invention is an amount that is sufficient to decrease the degree of, or inhibit or prevent, the functional interaction of an α2I domain-containing integrin and one or more of the targets that would have interacted with that integrin in the absence of the peptide of the invention.

A "pharmaceutically acceptable salt" is intended to include salts formed from pharmaceutically acceptable acids or bases, such as, for example, but not limited to, acids such as sulfuric, hydrochloric, nitric, phosphoric, etc., or bases such as alkali or alkaline earth metal hydroxides, ammonium hydroxides, alkyl ammonium hydroxides, etc.

The term "pharmaceutically acceptable vehicle" is intended to include solvents, carriers, diluents, and the like, which are utilized as additives to preparations of the invention so as to provide a carrier or adjuvant for the administration of such compounds.

While the discussion and exemplification below are often presented using the human integrin proteins, the peptides and methods of the invention are useful in any species sensitive to snake bites in which jararhagin is an active component of the venom, as such activity is evidence of the ability the peptides of the invention to bind the target integrin in such species. Therefore, discussion and exemplification using the human embodiment below is not intended to limit the invention in this regard.

Collagen recognition by integrins resembles integrin-fibronectin binding. Not only do collagen-binding αI domains and RGD-binding putative βI domains have structural similarities but also cyclic RGD peptides can bind α2β1 integrin. The three collagen amino acid residues thought to be important for integrin binding to collagen contain two aspartic acids and one arginine.

The inventors hypothesized that the motif in jararhagin that blocks rα2I domain binding to collagen must contain either aspartic acid or arginine residues and that the critical motif for such action would be in a hydrophilic loop as the known integrin recognition sites in matrix molecules or in snake venom disintegrins are in hydrophilic loops. The inventors searched for previously unknown sequences in the jararhagin structure that fulfilled these criteria and prepared synthetic peptides for testing in solid phase binding assays with integrin rα2I domain.

One of the peptides derived from the metalloproteinase domain, CTRKKHDNAQC (SEQ ID No. 5) containing amino acids 241–249 (the terminal cysteines at either end have been added to the native sequence) in the metalloproteinase domain of jararhagin, was found to strongly bind to rα2I domain. The high binding affinity was evidenced by the fact that when europium-labeled rα2I (recombinant α2I) domain had adhered to the peptide there was no detectable detachment during a two hour follow-up period, even when a 10-fold excess of unlabeled rα2I domain had been added to the assay.

Of the peptides tested, the same peptide was also the only one that inhibited rα2I domain adhesion to collagens of type I and IV and to laminin-1. Furthermore, the peptide competed with *B. jararaca* venom in rα2I domain binding. Thus, the inventors concluded that the presence of an amino acid sequence corresponding to the above amino acids 241–249 is a reason why jararhagin interacts with α2β1 integrin.

Mutational analysis of the peptide sequence revealed a novel integrin binding motif RKK or RKKH (SEQ ID No. 8). Histidine, the fourth amino acid in the RKKH sequence, may also be important for the full function. Surprisingly, the mutation of aspartic acid in the peptide sequence had no effect. The known matrix molecule ligands for α2β1 integrin do not contain the RKK(H) sequence.

The novel rα2I domain binding motif found above, or peptides containing the same, can prevent matrix protein recognition. Without intending upon being held to this explanation, this effect is thought to occur by either direct interaction with the I domain ligand binding site or by causing a change in I domain conformation and thus masking the ligand recognition site. The peptide-dependent alteration in the conformation of rα2I domain was evident in experiments showing that concomitant with the prevention of collagen binding, the peptide induced the attachment of rα2I domain to echovirus-1. This also indicates that the occupancy of one ligand recognition site can regulate the affinity of another site.

Accordingly, each of the novel integrin binding proteins of the invention comprises a colinear sequence of three amino acids, arginine-lysine-lysine (RKK), that, when the peptide is in the cyclic form, imparts integrin binding activity to the peptide. One, two, three or more copies of the RKK sequence motif may be present within the sequence of the peptide, such copies being sufficient to provide the peptide with the ability to decrease the interaction of integrin with collagen.

In a first embodiment, the peptides of the invention are cyclic peptides that contain the amino acid sequence $X_1RKKX_2X_3X_4X_5X_6$ (SEQ ID No. 1) wherein each X is an amino acid and amino acids $X_1$–$X_6$ are any amino acid (especially A, R, N, D, C, Q, E, G, H, I, L, K, MF, P, S, T, W, Y or V) but preferably $X_2$ is histidine (H).

In a further embodiment, the peptides of the invention are cyclic peptides that contain the amino acid sequence $X_1RKKX_2X_3X_4X_5$ (SEQ ID No. 2), wherein amino acids $X_1$–$X_5$ are any amino acid as above but preferably $X_2$ is histidine (H).

In a further embodiment, the peptides of the invention are cyclic peptides that contain the amino acid sequence $X_1RKKX_2X_3X_4$ (SEQ ID No. 3), wherein amino acids $X_1$–$X_4$ are any amino acid as above but preferably $X_2$ is histidine, and in which peptide has a cyclic structure, as above.

In a highly preferred embodiment, the peptide of the invention is a cyclic peptide that has the amino acid sequence CTRKKHDNC (SEQ ID NO. 4) or a cyclic peptide that has the amino acid sequence CTRKKHDNAQC (SEQ ID NO. 5), and preferably the two terminal cysteine residues are involved in forming a disulfide bridge that imparts a cyclic structure to the peptide.

The cyclic peptides of the invention can lack one or more of the amino acids X as written above, and especially one or more of C, T, H, D, N, A and/or Q. Further, the cyclic peptides of the invention can contain additional amino acids either inserted into the above sequences, and/or flanking the above sequences, as long as the RKK motif remains colinear, provided that such peptides retain the ability to bind α2-integrin.

The terminal cysteine residues need only be located in a manner that will result in the cyclization of the peptide. Preferably, the cysteines are placed at the terminal ends of the peptide, so that disulfide bond formation results in the proper size loop so as to impart the biological activity to the circular form of the peptide. However, one or both of the cysteines residues can be internal to the peptide, rather than on the end, and any "tail" that extends beyond the cysteine is not likely to pose a problem as long as it does not contribute to the loss of circular form of the remaining peptide. In that regard, as long as the cyclic form of the peptide was not hindered, so that it was in a conformation that allowed it to remain biologically active, then a different moiety, for example a protein such as albumin, could be used as a linker, spacer, or attached to the end of the cyclic peptide, so as to attach the cyclic peptide of the invention to a solid support, or other desired moiety, for example, a detectable label.

When the cysteines are on the terminal ends of the peptide, the peptide preferably contains nine amino acids between the cysteines. Eight amino acids did not enhance the activity and thus is also useful in this regard. A cyclic peptide with seven amino acids between the terminal cysteines was about 20 times more effective than those with seven or eight amino acids, and thus is especially preferred. Generally, peptides that contain 10 or more amino acids between the terminal cysteines run the risk of behaving more like a (nonfunctional) linear molecule rather than a circular one. Cyclic peptides that contain five or fewer amino acids between the terminal cysteines are very difficult, if not impossible, to prepare. Accordingly, a cyclic peptide that contains seven amino acids between terminal cysteines is the most preferred embodiment.

The sequence of the peptide of the invention is intended to encompass variants of the above-described peptides, such variants having amino acid substitutions of inconsequential difference, for example, the substitution of one basic amino acid for another (except in the RKK motif), the substitution of one hydrophobic reside for another, the substitution of one neutral residue for another, the substitution of one acidic residue for another, or the substitution of one aromatic residue for another.

In the preferred embodiment, the cyclic form of the peptide results from a disulfide bridge. However, any covalent bond that results in the cyclic form of the peptide is expected to be useful as the function of the bridge is simply to force the peptide in the proper conformation.

As it known in the art, the amino acid residues can be in their protected or unprotected form, using appropriate amino or carboxyl protecting groups. Useful pharmaceutically acceptable cations include alkali or alkaline earth metallic cations (for example, Na, K, Li, ½ Ca, ½Ba, etc.) or amino cations (for example tetraalkylammonium, trialkyl ammonium, where each alkyl group can be $C_1$–$C_{12}$, but preferably is a $C_1$–$C_6$ branched or unbranched alkyl group). Pharmaceutically acceptable lower alkyl esters, pharmaceutically acceptable amides and pharmaceutically acceptable acid addition salts can also be prepared.

The peptides of the invention can by synthesized, and cyclized, using methods known in the art, for example as described in U.S. Pat. No. 5,627,263, incorporated herein by reference.

The cyclic integrin binding peptides according to the present invention are 5 useful as blockers (inhibitors) of integrin function, especially human integrin function. Integrin binding to its native ligands is inhibited or prevented in the presence of the peptides of the invention. Especially, the cyclic integrin binding peptides are useful for blocking integrin α2I domain interaction with macromolecules that interact with this domain, for example, collagens such as collagens I and IV and, for example, laminin- 1.

The sequence of the human recombinant α2I domain is provided in Takada, Y. and M. E. Hemler, *J. Cell Biol.* 109:397–407 (1989) (incorporated herein by reference). The α2I domain can be produced using common recombinant hosts, for example, *E. coli*. Its properties can be characterized using a sensitive solid phase assay based on the europium labeling of the rα2I domain and time resolved fluorescence measurements. The assay makes it possible to measure directly the binding of rα2I domain without the presence of enzymes or other large molecules linked to it.

The α2-integrin binding ability of a peptide of the invention can be determined using any assay that detects such binding, and especially that detects the ability of such binding to block integrin interaction with collagen I, collagen IV or laminin-1. As exemplified below, a binding assay using europium labeled recombinant α2I domain (Example 2), and an assay that detects activation of the virus-1 recognition site in the α2I domain, are useful in this regard (Example 2).

The peptides of the invention are especially useful for inhibiting or preventing the migration of cells on collagen, in vivo or in vitro. The ability of a peptide of the invention to block cell migration can be determined using the cell migration assays as provided in Example 7. Thus, the present invention provides methods for inhibiting cell migration on collagen in vitro, and in vivo in a patient in need of treatment to inhibit the same, when such migration is mediated in an integrin-dependent manner. The invention thus provides a therapeutic method of treating diseases, including periodontitis, where cell migration is a part of the pathogenic mechanism.

The invention further provides a method for inhibiting the migration of malignant cells, and therefor, for treating diseases characterized by the same, for example, cancers, including osteosarcoma, and melanoma, especially where α2β1 integrin dependent cell migration may contribute to the malignant mechanism.

This invention further provides a method of inhibiting adhesion of platelets to collagen and collagen-induced platelet aggregation. The ability of a peptide of the invention to inhibiting cell adhesion can be determined as provided in Example 8. Thus, the invention provides a method for treating patients in need of preventative or ameliorative treatment for conditions or diseases such as cardio-vascular diseases that are characterized by a need to prevent adhesion of platelets to collagen and collagen-induced platelet aggregation, for example, in stroke victims or patients at risk of having a stroke.

Pharmaceutical preparations containing the peptides of the invention can contain inter alia, pharmaceutically acceptable carriers for the stabilization and effective formulation of the peptides, suitable vehicles, and their formulation, inclusive of other human proteins, for example, human serum albumin, are described, for example, in Remington's Pharmaceutical Sciences (18th edition, A. R. Gennaro, ed., Mack Publishing, Easton, Pa. 1990). In order to form a pharmaceutically acceptable composition that is suitable for administration of efficacious amounts of the peptides of the invention to a patient in need of such composition, such composition will contain an effective amount of one or more of the peptides of the invention, together with a suitable amount of carrier vehicle if desired.

The peptides of the invention preferably have been purified so as to be substantially free of contaminants. A material is said to be "substantially free of contaminants" if it has been substantially purified from undesired material with which it had been associated when synthesized, either in the cell or in an in vitro system, to a degree sufficient to make it useful for a desired purpose.

Compositions useful in the methods of the invention can contain one or more of the peptides of the invention. When more than one of the peptides is present in the composition, it may be part of the same amino acid chain as the another peptide, or be present as a separate peptide in the composition. Compositions for intravenous, intramuscular or subcutaneous administration preferably administer dosages in the range of from about 1 pg/kg body weight to 1 mg/kg body weight although lower or higher doses can be administered. The required dosage will depend upon the severity of the condition of the patient, for example, and such criteria as the patient's weight, sex, age, and medical history. The dose can also vary depending upon whether it is to be administered in a veterinary setting to an animal or to a human patient.

For the purposes of parenteral administration, compositions containing the peptides of the invention are preferably dissolved in distilled water and the pH preferably adjusted to about 6 to 8. If the peptide is to be provided in a lyophilized form, lactose can be added to the solution to facilitate the lyophilization process. In such form, the solution is then sterilized, introduced into vials and lyophilized.

Useful preparations of the compositions of the invention for parenteral administration also include sterile aqueous and non-aqueous solvents, suspensions and emulsions. Examples of useful non-aqueous solvents include propylene glycol, polyethylene glycol, vegetable oil, fish oil, and injectable organic esters. Examples of aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Examples of intravenous vehicles include fluid and nutrient replenishers, electrolyte replenishers, such as those based upon Ringer's dextrose and the like.

Injectable preparations, such as oleaginous solutions, suspensions or emulsions, may be formulated according to known art, using suitable dispersing or wetting agents and suspending agents, as needed. When the active compounds are in water-soluble form, for example, in the form of water soluble salts, the sterile injectable preparation may employ a nontoxic parenterally acceptable diluent or solvent as, for example, sterile nonpyrogenic water or 1,3-butanediol. Among the other acceptable vehicles and solvents that may be employed are 5% dextrose injection, Ringer's injection and isotonic sodium chloride injection (as described in the USP/NF). When the active compounds are in a non-water soluble form, sterile, appropriate oily suspensions containing suitable lipophilic solvents or vehicles, such as fatty oil, for example, sesame oil, or synthetic fatty acid esters, for example, ethyl oleate or triglycerides, are used. Alternatively, aqueous injection suspensions which contain substances which increase the viscosity, for example, sodium carboxymethyl cellulose, sorbitol, and/or dextran, and optionally also contain stabilizers may be used.

For iontophoretic delivery of a peptide of the invention, the peptide preferably has a pH of about 4.0 or less or a pH of about 7.0 or greater. Methods of iontophoresis are known, for example as described in U.S. Pat. No. 5,637,084 and in U.S. Pat. No. 4,950,229, both incorporated herein by reference.

Pharmaceutical preparations for oral (but systemic) administration can be obtained by combining the active compounds with solid excipients, optionally granulating a resulting mixture and processing the mixture or granules, after adding suitable auxiliaries, if desired or necessary, to give tablets of dragee cores. Pharmaceutical preparations for treatment of periodontitis can be administered in a composition that remains in the oral cavity, preferably by placing the preparation directly into the periodontal cavity, and most preferably in a sustained release form. Alternatively, the preparation can be painted on the teeth and/or gums, so as to locally release the peptide at the desired site. Such teachings are provided in U.S. Pat. No. 5,002,769, U.S. Pat. No. 5,023,082, U.S. Pat. No. 5,160,737, U.S. Pat. No. 5,330,746, U.S. Pat. No. 5,425,953, U.S. Pat. No. 5,438,076 and U.S. Pat. No. 5,639,795 each incorporated herein by reference. The preparation can also be provided on a membrane.

Suitable excipients are, in particular, fillers such as sugars, for example lactose or sucrose, mannitol or sorbitol, cellulose preparations and/or calcium phosphates, for example tricalcium phosphate or calcium hydrogen phosphate, as well as binders, such as starch, pastes, using, for example, maize starch, wheat starch, rice starch, or potato starch, gelatine, tragacanth, methyl cellulose, hydroxypropylmethyl cellulose, sodium carboxymethyl cellulose, and/or polyvinyl pyrrolidone, and/or, if desired, disintegrating agents, such as the above-mentioned starches, and also carboxymethyl-starch, cross-linked polyvinyl pyrrolidone, agar or alginic acid or a salt thereof, such as sodium alginate. Auxiliaries are, above all, flow-regulating agents and lubricants, for example, silica, talc, stearic acid or salts thereof, such as magnesium stearate or calcium stearate, with suitable coating, which if desired, are resistant to gastric juices and for this purpose, inter ala concentrated sugar solutions, which optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetyl cellulose phthalate or hydroxypropylmethyl cellulose phthalate, are used. Dyestuffs or pigments may be added to the tablets or dragee coatings, for example, for identification or in order to characterize different combinations of active compound doses.

Solid dosage forms for oral administration include capsules, tablets, pills, troches, lozenges, powders and granules. In such solid dosage forms, the active compound may be admixed with at least one inert diluent such as sucrose, lactose or starch. Such dosage forms may also comprise, as is normal practice, pharmaceutical adjuvant substances, e.g., stearate lubricating agents. Solid oral preparations can also be prepared with enteric or other coatings which modulate release of the active ingredients.

Liquid dosage forms for oral administration include pharmaceutically acceptable emulsions, solutions, suspensions, syrups and elixirs containing inert nontoxic diluents commonly used in the art, such as water and alcohol. Such compositions may also comprise adjuvants, such as wetting agents, emulsifying, suspending, sweetening, flavoring and perfuming agents.

The compositions of the invention may also be administered by means of pumps, or in sustained-release form. The compounds of the invention may also be delivered to specific organs in high concentration by means of suitably inserted catheters, or by providing such molecules as a part of a chimeric molecule (or complex) which is designed to target specific organs. In this regard, the peptides above can form a cyclic "loop" on the end of a longer peptide, such peptide having a second domain that possesses a desired activity. Such fusion proteins can be designed to provide a domain that assists in killing a cell that contains a membrane-bound integrin that binds the cyclic peptide of the invention.

Administration in a sustained-release form is more convenient for the patient when repeated injections for prolonged periods of time are indicated so as to maximize the comfort of the patient. Controlled release preparation can be achieved by the use of polymers to complex or adsorb the peptides of the invention. Controlled delivery can be achieved by selecting appropriate macromolecules (for example, polyesters, polyamino acids, polyvinyl pyrrolidone, ethylenevinylacetate, methylcellulose, carboxymethylcelluloase protamine zinc and protamine sulfate) as well as the method of incorporation in order to control release. Another possible method to control the duration of action by controlled release preparations is to incorporate the desired peptide into particles of a polymeric material such as polyesters, polyamino acids, hydrogels, poly (lactic acid) or ethylene vinylacetate copolymers. Alternatively, instead of incorporating the peptide into these polymeric particles, the peptides can be entrapped into microparticles, prepared, for example, by coacervation techniques or by interfacial polymerization, for example, hydroxymethylcellulose or gelatin-microcapsules and poly (methylmethacrylate) microcapsules, respectively, or in colloidal drug delivery systems, for example liposomes, albumin microspheres, microemulsions, nanaparticles, and nanocapsules or in macroemulsions.

The biological half-life of the peptide of the invention can be lengthened by increasing the retention or stability of the cyclic form in the desired environment. Especially agents that enhance the stability of the cyclic form can be expected to enhance the biological half-life of the peptide. In that regard, the use of one or more D-amino acids (especially if substituted for the same L-amino acid at that position), or the use of one or more amino acid analogs, such as penicillamine (3-mercaptovaline) in the peptide structure may be placed such that the D-amino acid or amino acid analog interfere with the metabolic breakdown of the cyclic structure in the animal or patient being administered the composition, or in the desired in vitro composition.

The use of D-amino acids or amino acid analogs to increase the binding of the peptide of the invention to the target, especially to integrins containing the α2I domain, is also contemplated.

The peptides that are used in the compositions and methods of the invention can be employed in dosage forms such as tablets, capsules, powder packets, or liquid solutions for oral administration if the biological activity of the material is not destroyed by the digestive process and if the characteristics of the compound allow it to be absorbed across the intestinal tissue.

The pharmaceutical compositions of the present invention can be manufactured in a manner which is in itself know, for example, by means of conventional mixing, granulating, dragee-making, dissolving, lyophilizing or similar processes.

The peptide of the invention can also be used as affinity reagents for the extraction of ligands that bind to them, especially for the extraction of α2I-containing integrins from a mixture.

Having now fully described the invention, the same will be more readily understood by reference to specific examples which are provided by way of illustration, and are not intended to be limiting of the invention, unless specified.

EXAMPLES

Example 1
Generation of Human Recombinant Integrin α2I Domain

DNA encoding α2I domain was generated by PCR using human integrin α2 cDNA as a template (Integrin α2 cDNA was a gift from Dr. M. Hemler, Dana-Farber, Boston). The forward primer was 5'-CACAGGGATCCCCTGATTTTCAGCTC-3' (SEQ ID No. 9) and the reverse primer was 5'-GTGGCTGAATTCAACAGTACCTTCAATG-3' (SEQ ID No. 10). Primers were designed to introduce two restriction sites in the product: BamHI-site in the 5'-end and EcoRi-site in the 3'-end. PCR-product and pGEX2T (Pharmacia) were digested with BamHI and EcoRi, ligated and transformed into E. coli DHα5F' cells. Plasmid having α2I domain insert (pJKα2I) was then sequenced and transformed into E. coli BL21 for production of recombinant protein rα2I. Production and purification of glutathione S-transferase-rα2I fusion protein were carried out as follows: typically 400 ml LB (carbenicillin 50 μg/ml) was inoculated with 40 ml overnight culture of BL21/pJKα2I and the culture was grown for 1 h at 37° C. Then an inducer, IPTG (final concentration 0.1 mM) was added for 4 h.

Human recombinant integrin α2I was purified from the E. coli cells as follows. Cells were harvested by centrifugation and pellets were resuspended in phosphate buffered saline (PBS, pH 7.4). Suspensions were sonicated, centrifuged and supernatant was retained. Pellets were resuspended in PBS, sonicated and centrifuged a further two times and supernatants were pooled. Glutathione Sepharose® (Pharmacia) was added and the resulting lysate was incubated at room temperature for 30 min by gently agitation. The lysate was centrifuged, the supernatant fraction was removed and glutathione Sepharose® with bound fusion protein was transferred into the suitable column. The column was then washed with 10 volumes PBS (140 mM NaCl, 2.7 mM KCl, 10 mM $Na_2HPO_4$, 1.8 mM $KH_2PO_4$, pH 7.3) and the fusion protein was eluted with glutathione eluting buffer (Pharmacia; 10 mM reduced glutathione in 50 mM Tris-HCl, pH 8.0). The fusion protein was cleaved with thrombin protease (Pharmacia; 10 units) for at least two hours at room temperature and was dialysed against PBS to remove glutathione. The cleavage mixture was passed a second time down the glutathione Sepharose® column to remove glutathione S-transferase.

The rα2I was collected from the flowthrough. It was necessary to treat the recombinant protein with 5 mM dithiothreitol (DTT) to allow proper folding (5 mM DTT in PBS), since when analyzed by native PAGE, extra bands were seen without the treatment. The recombinant protein was at least 90% pure by SDS-PAGE (polyacrylamide gel electrophoresis) and only a single band was observed by native-PAGE.

The recombinant α2I domain produced was 223 amino acids long having two non-integrin amino acids in the amino terminal (GS) integrin amino acids corresponding to integrin sequence 124–339 (PDFQ . . . IEGTV) (SEQ ID No. 11 and SEQ ID No. 12) and six non-integrin amino acids in the carboxyl terminal (EFIVTD; SEQ ID No. 13).

Example 2
Binding Assay for Europium Labeled rα2I

Venom from Bothrops jararaca pit viper prevents the binding of recombinant integrin α2I domain to type I collagen A sensitive solid-phase rα2I ligand binding assay based on the use of europium labeled rα2I was developed. Labelling of rα2I with europium was carried out as follows: 1/20 volume 1M $NaHCO_3$ (pH 8.5) was added to the purified rα2I to elevate the pH for labelling with isotiocyanate. The europium labelling reagent (Wallac) was added at 100-fold molar excess and incubated overnight at +4° C. The unbound label was removed by gel filtration on a Sephadex G50/Sepharose 6B column (Pharmacia) and the fractions containing the labeled protein were pooled.

A 96-well immunoplate (Maxisorp, Nunc) was coated by exposing the surface of its well to 0.1 ml of PBS containing 5 μg/cm² of the plate surface, type I collagen (bovine dermal, Cellon), type IV collagen (Sigma), laminin-1 (purified from basement membranes of the Engelbreth-Holm-Swarm mouse tumor, Collaborative Research), fibronectin (human plasma fibronectin, Boehringer Mannheim) or 3.3 μg/ml echovirus-1 or echovirus-7 for 12 h at +4° C. Alternatively peptides and B. jararaca venom (Sigma) were coated at various concentrations on 96-well amine binding plates (Costar) according to the manufacturer's instructions.

Residual protein absorption sites on all wells were blocked with 0.1% heat inactivated bovine serum albumin in PBS for 1 h at +37° C. Echoviruses 1 (Farouk strain) and 7 (Wallace) were obtained from the ATCC. The purified viruses were diluted in PBS containing 0.5 mM $MgCl_2$ and stored at −70° C. until used. Europium labeled rα2I was added at a concentration of 500 ng/ml in PBS, 2 mM $MgCl_2$, 1 mg/ml BSA to the coated wells and incubated for 3 h at +37° C. Wells were then washed three times with PBS, 2mM $MgCl_2$. 0.1 ml Delfia enhancement solution (Wallac) was added to each well and europium signal was measured with fluorometry (Model 1232 Delfia, Wallac).

Figure 1B:
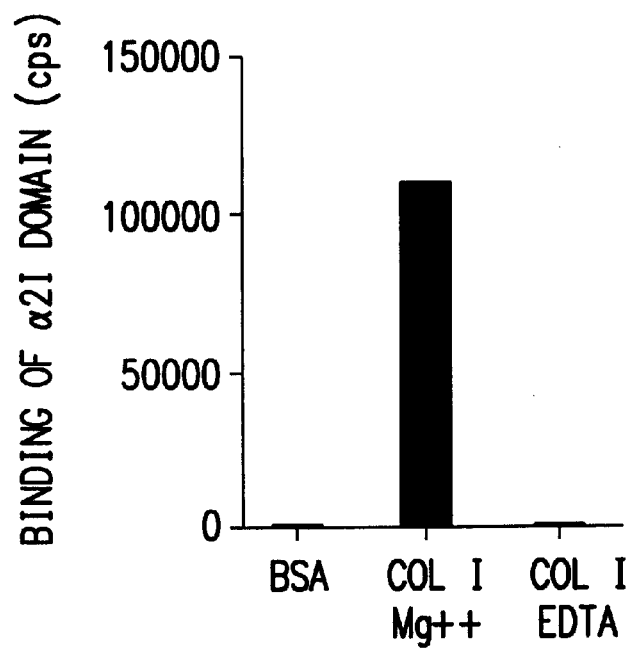
Figure 1C:
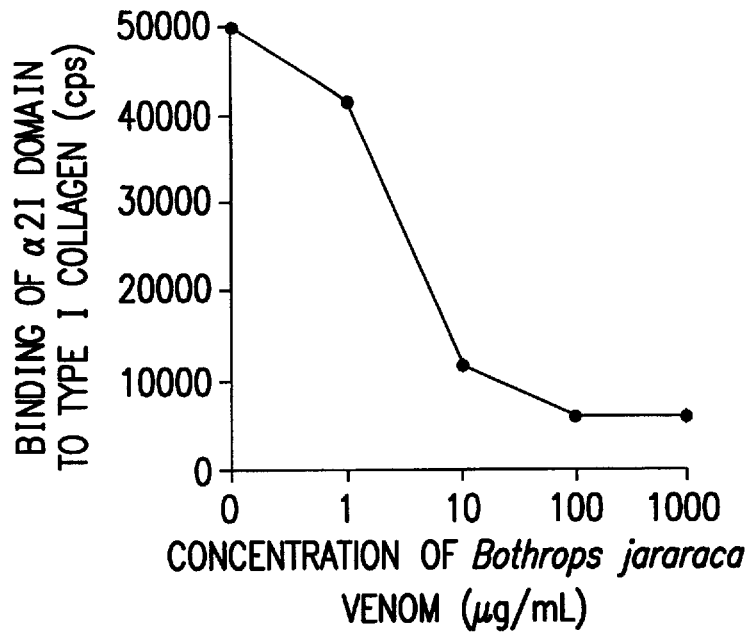

When peptides were added endogenously, the lyophilized peptides were solubilized directly to the europium labeled rα2I 500 ng/ml in PBS, 2 MM $MgCl_2$, 1 mg/ml BSA and then added to wells. When EDTA was used instead of $MgCl_2$, europium labeled rα2I was diluted to PBS, 2 mM EDTA and subsequent washes were performed with this buffer. This binding assay was found to be very sensitive, making it possible to reduce the amount of rα2I domain used in the experiments. Furthermore, the small size of europium suggests that the measurements are more reliable than with larger marker molecules. Thirdly, the microtiter well assay described here was found to be usable for screening of large numbers of putative integrin rα2I domain blocking molecules.

rα2I bound type I collagen, type IV collagen, and laminin-1. However, it did not significantly bind to fibronectin or albumin (FIG. 1A). rα2I bound type I collagen in a $Mg^{++}$ dependent manner and the addition of 2 mM EDTA abolished binding completely (FIG. 1B). This is consistent with the fact that α2β1 interacts with collagen only in the presence of divalent cations. The binding of rα2I domain to echovirus-1 was much weaker than to the matrix molecules.

Previous studies have shown that B. jararaca venom inhibits the interaction of platelet α2β1 integrin with collagen (De Luca, M. et al., Biochem. Biophys. Res. Commun 206:570–576 (1995)). However, it was unknown whether this inhibitory action was due to the prevention of the α2I domain function. Also, the epitopes involved in the interaction were not known.

Figure 1D:
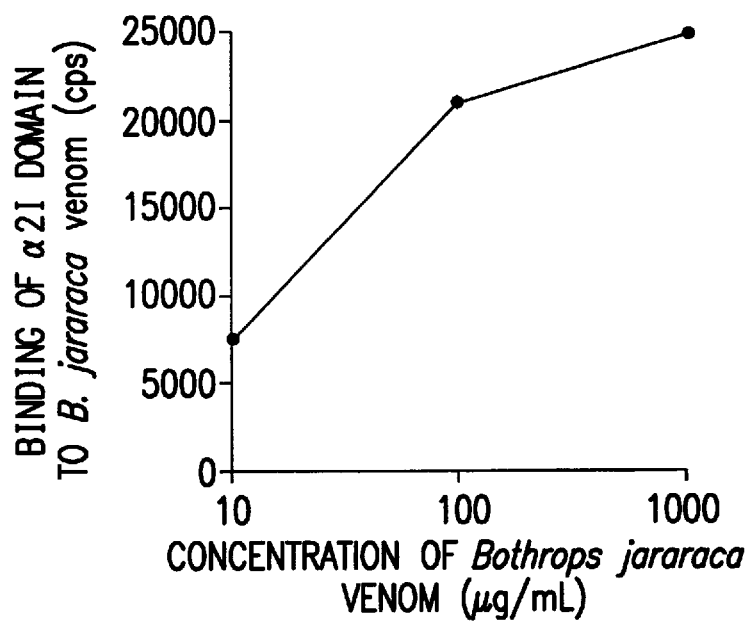

The effects of B. jararaca venom to the binding of rα2I domain to type I collagen were investigated using the solid-phase ligand binding assay described above. Europium labeled rα2I domain was allowed to attach to collagen I substratum in the presence of 2 mM $Mg^{++}$ and the amount of bound rα2I was then determined. The effect of the venom was tested with concentrations ranging from 1 μg/ml–1000 μg/ml. The venom inhibited the rα2I domain-collagen interaction efficiently and in a concentration dependent manner (FIG. I C). To determine if the inhibition seen was due to the direct interaction of rα2I with the snake venom microtiter wells were coated with the venom proteins and tested rα2I binding to this substratum. rα2I was found to bind the venom directly in a concentration dependent manner (FIG. 1D). According to published literature it is evident that jarrhagin is the protein in B. jararaca venom inhibiting the binding of α2β1 integrin to collagen (De Luca, M. et al., Biochem. Biophys. Res. Commun. 206:570–576 (1995)) and therefore most probably the venom component binding to rα2I domain.

Example 3
Peptides and Binding Assay Using Biotinylated 229ox

A short, cyclic jararhagin derived peptide mimics the effect of B. jararaca venom on integrin rα2I domain-collagen interaction The characterization of the α2I domain binding site in jararhagin was continued through the use of a series of short cyclic peptides corresponding to regions along the protein. The tested regions were selected based on the following: i) Integrin binding motifs in matrix proteins and in snake venom disintegrins are found in loop structures. ii) The known integrin binding motifs contain aspartic acid residue. iii) The published model of integrin-collagen interaction emphasizes the role of arginine residue in addition to aspartic acid residue.

The jararhagin-derived peptides were designed based on the secondary structure prediction of jararhagin amino acid sequence. Secondary structure prediction was performed using the Peptide structure program from Genetics Computer Group (GCG) Software package (Madison, Wis.). Surface probability according to the Emini method (Emini, E. A. et al., J. Virol. 55:836–839 (1985)) and hydrophilicity according to the Kyte-Doolittle (Kyte, J. et al., J. Mol. biol. 157:105–132 (1982)) method were taken into account.

The peptides were synthesized on an automated peptide synthesizer (Applied Biosystems 431A) using 9-fluorenyl methoxycarbonyl (Fmoc) chemistry. The peptides for the alanine substitution series were purchased from Research Genetics (Huntsville, Ala.). After synthesis the peptides were oxidized to form disulphide bridges. The peptides were solubilized at 1 mg/ml concentration to 0.1 M ammonium carbonate buffer and incubated for 16–24 h at +4° C. The oxidation was checked with reverse-phase HPLC and the oxidized peptides were lyophilized.

All the peptides were fully soluble at 10 mg/ml in PBS. Since the highest concentration used was 1 mg/ml, non-specific effects due to insoluble peptides were avoided. The isoelectric points (PI) of the various peptides was also determined from the primary sequence using the Isoelectric program from Genetics Computer Group (GCG) Software package (Madison, Wis.). Peptide 225ox (Table 1) was found to have a similar isoelectric point than 229ox (Table 1) and was therefore chosen to be the control peptide in some experiments.

Biotinylation of 229ox was carried out as follows: lyophilized 229ox peptide was solubilized in PBS and 1/5 volume 0.1 M $NaHCO_3$, 0.5 M NaCl (pH 8.0) was added to elevate the pH for biotinylation. Sulpho-NHS-biotin (Calbiochem) was added 1:2 (w/w) 229ox:biotin and incubated for 2 h RT. 1/10 volume 0.5 M Tris-HCl (pH 8.0) was added to end the biotinylation reaction.

For the binding assays using biotinylated 229ox peptide 96-well amine binding plates (Costar) were coated with various concentrations of rα2I domain or rα2I domain-derived peptides according to manufacturer's instructions. Residual protein absorption sites on all wells were blocked with 0.1% heat inactivated bovine serum albumin in PBS for 1 h at +37° C. 100 μM biotinylated 229ox in PBS, 2 mM $MgCl_2$, 1 mg/ml BSA was added to the coated wells and incubated for 3 h at +37° C. Wells were then washed three times with PBS, 2mM $MgCl_2$ and europium labeled streptavidin (Wallac) was added at a concentration of 500 ng/ml in PBS, 2 mM $MgCl_2$, 1 mg/ml BSA for 30 min at room temperature. Wells were again washed three times. 0.1 ml Delfia enhancement solution (Wallac) was added to each well and europium signal was measured with fluorometry (Model 1232 Delfia, Wallac). When EDTA was used instead of $MgCl_2$, europium labeled rα2I was diluted to PBS, 2 mM EDTA and subsequent washes were performed with this buffer.

Peptides corresponding to the selected sequences were synthesized and the resulting peptides are summarized in Table I.

Figure 2A:
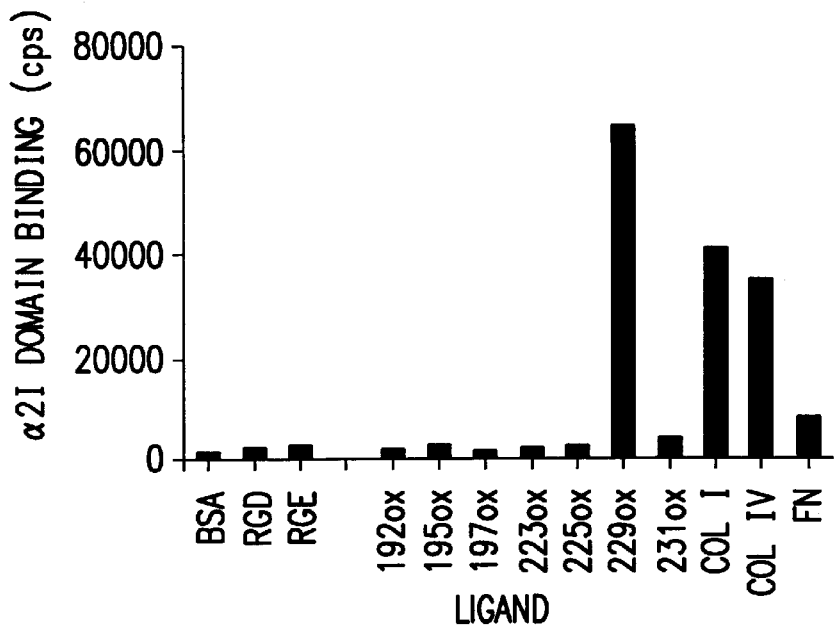
FIGS. 2(A–B). Binding of europium labeled rα2I to adhesion proteins and jararhagin-derived peptides in a solid phase assay. Microtiter plate wells were precoated with various peptides, type I collagen, type IV collagen and fibronectin. The data represent the mean from three parallel experiments showing rα2I binding to different substrata (A). Microtiter plate wells were precoated with BSA and type I collagen and rα2I was allowed to attach for 3 h in the presence of peptide (B).

To investigate if any of these peptides could directly interact with α2I domain, the jararhagin peptides along with cyclic RGD peptide, type I collagen, type IV collagen, and fibronectin were coated to microtiter wells and rα2I-Eu was added. The results show that one of the jararhagin peptides, denoted 229ox, bound to rα2I-domain efficiently while the other peptides tested showed no effect (FIG. 2A).

Figure 2B:
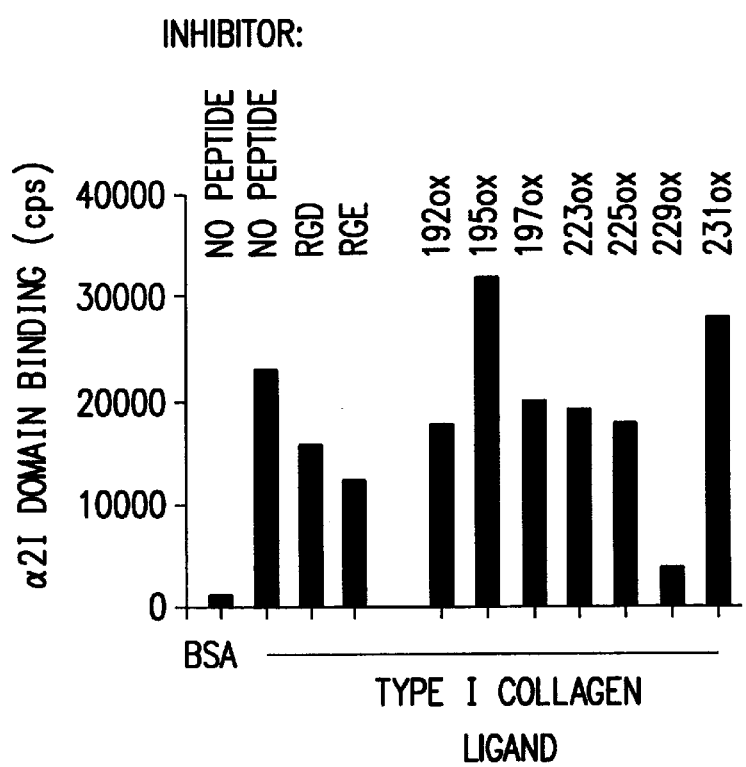
Figure 3:
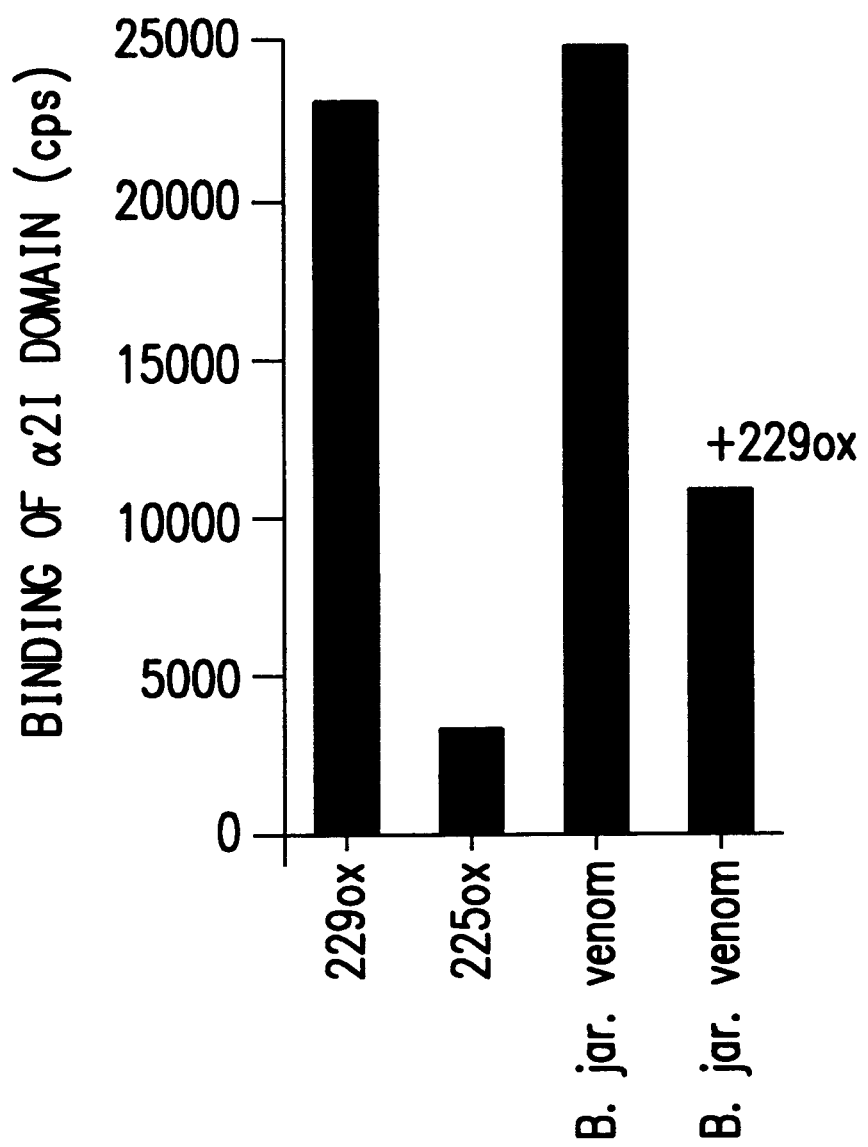
FIG. 3. Attachment of rα2I to peptides and *Bothrops jararaca* venom in the presence of 229ox peptide. Microtiter plate wells were precoated with peptide or *Bothrops jararaca* venom. rα2I domain was allowed to bind in the presence or absence of 229ox peptide. The data represent the mean from three parallel experiments.

The peptides were then tested for their ability to influence rα2I binding to type I collagen at a concentration of 500 μM. Again only peptide, 229ox, had significant effect: it almost completely inhibited the interaction between rα2I domain and collagen (FIG. 2B).

TABLE I

Sequences of the synthetic peptides used in this study. The name and the position of the peptides synthesized based on the primary sequence of jararhagin (Paine, M. J. I. et al., J. Biol. Chem 267:22869–22876 (1992) and α2I domain (Takada, Y. and Hemler, M. E., J. Cell Biol. 109:397–407 (1989) is shown.

| Jararhagin peptides | Amino acid sequence | Residue no. |
|---|---|---|
| 192ox; SEQ ID No. 14 | CWSNGDKITC* | 212–219 |
| 195ox; SEQ ID No. 15 | CEQQRYDPYKC* | 151–159 |
| 197ox; SEQ ID No. 16 | CKLPDSEAHAC* | 103–111 |
| 223ox; SEQ ID No. 17 | CHYSPDGREIC* | 46–54 |
| 225ox; SEQ ID No. 18 | CPADVFHKNC* | 441–449 |
| 229ox; SEQ ID No. 5 | CTRKKHDNAQC* | 241–249 |
| 231ox; SEQ ID No. 19 | CYSNDDEHKGC* | 537–545 |

| I domain peptides | Amino acid sequence | Residue no. |
|---|---|---|
| P1; SEQ ID No. 20 | VCDESNSIYC* | 149–157 |
| P2; SEQ ID No. 21 | VCDESNSIYPWDAVKNC* | 149–164 |
| P3; SEQ ID No. 22 | IYPWDAVKNFLEKFVQG | 155–172 |
| P4; SEQ ID No. 23 | AVKNFLEKFVQGLDIG | 160–176 |
| P5; SEQ ID No. 24 | LDIGPTKTQVGLIQYA | 173–188 |
| P6; SEQ ID No. 25 | QYANNPRVVFNLNTYKTKEE | 186–205 |
| P7; SEQ ID No. 26 | LNTYKTKEEMIVAT | 197–210 |
| P8; SEQ ID No. 27 | ATSQTSQYGGDLTNT | 209–223 |
| P9; SEQ ID No. 28 | RKYAYSAASGGRRSAT | 231–246 |
| P10; SEQ ID No. 29 | TDGESHDGSMLKAVIDQ | 253–269 |
| P11; SEQ ID No. 30 | LDTKNLIKEIKAIASIPTER | 291–310 |
| P12; SEQ ID No. 31 | SDEAALLEKAGTLGEQ | 316–331 |

| Other peptides | Amino acid sequence | Reference |
|---|---|---|
| RGD | GACRGDCLGA*; SEQ ID No. 32 | Koivunen, E. et al., J. Biol. Chem. 268:20205–20210 (1993) |
| RGE | GACRGECLGA*; SEQ ID No. 33 | Koivunen, E. et al., J. Biol. Chem. 268:20205–20210 (1993) |

*Cyclic peptides

To show a correlation between the binding properties of the 229ox peptide and *B. jararaca* venom the ability of the 229ox peptide to compete with the rα2I binding site in the snake venom was tested. The results show that 229ox and *B. jararaca* venom both bind rα2I and that the 229ox rα2I indicates that 229ox represents the actual integrin binding site of jararhagin. Since the inhibition was not complete (about 50%) there is still a possibility, that *B. jararaca* venom contains also another binding site for α2I domain.

Figure 4A:
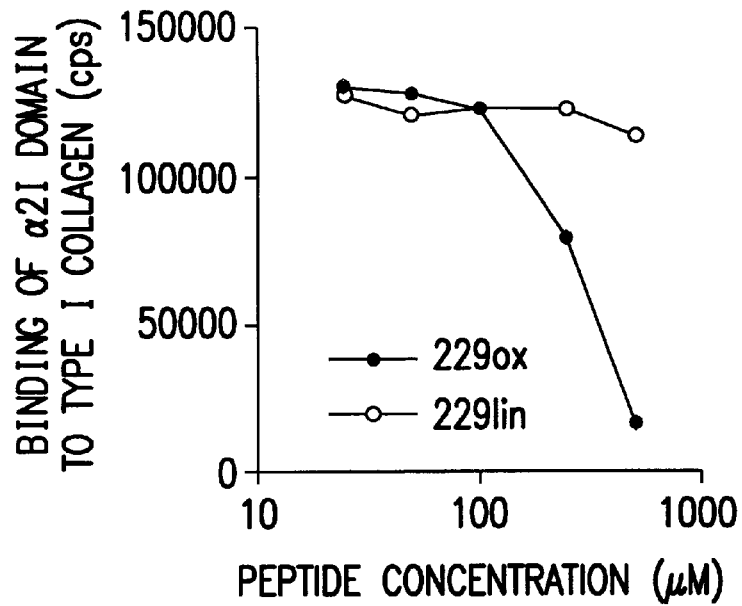
FIGS. 4(A–C). Properties of 229ox peptide. Dose response curves for inhibition of rα2I binding to type I collagen in the presence of cyclic or linear 229 peptide (A). Alternatively microtiter plate wells were precoated with 229ox peptide (B). 229ox peptide was added to rα2I binding assay on various precoated substrata (C).
Figure 4B:
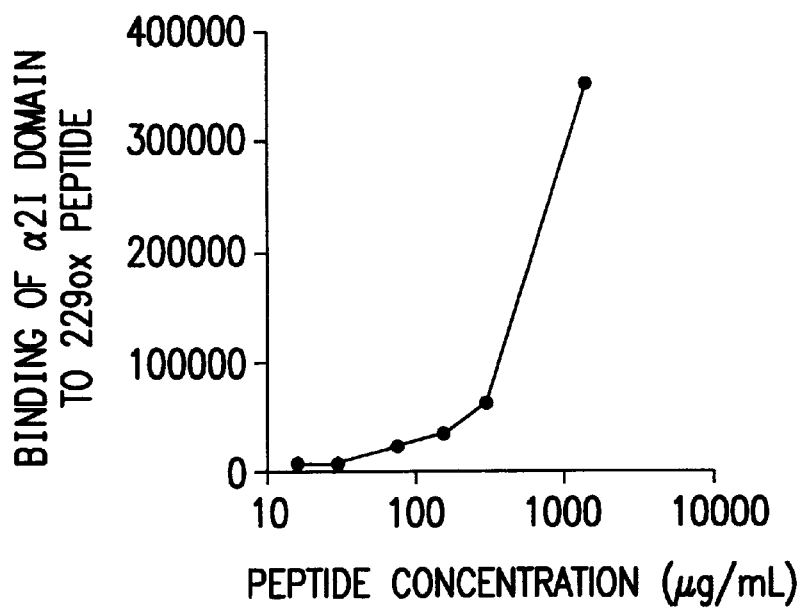
Figure 4C:
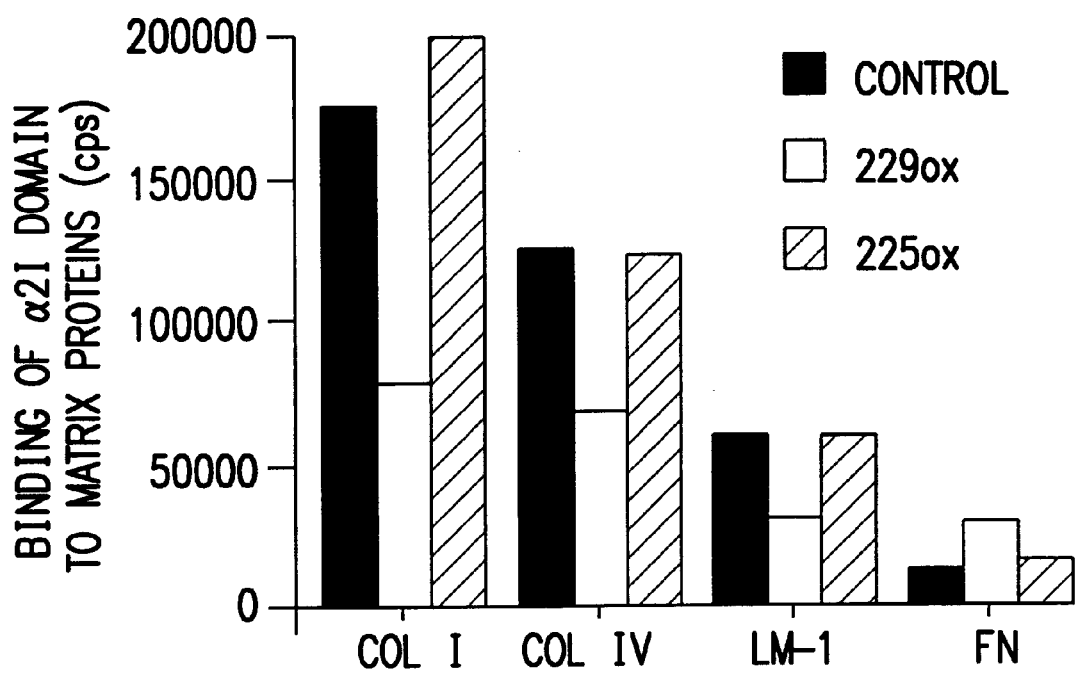

In a number of publications it has been shown that the cyclic structure of the integrin ligand mimicking synthetic peptide is often essential for high affinity binding. To test this, both oxidized and linear p229 peptide were used in the solid phase binding assay, supra. The cyclic 229ox showed the ability to inhibit rα2I adhesion to type I collagen, while the linear form of the peptide had only little effect (FIG. 4A). The binding of rα2I to solid phase bound 229ox was found to be concentration dependent and significant binding was observed at a coating concentration of 75 μg/ml (FIG. 4B). In addition to type I collagen rα2I domain binds also type IV collagen and laminin-1. The 229ox peptide inhibited the binding of rα2I to these ligands, while control peptide 225ox of the same length and conformation together with a similar pI value had no effect (FIG. 4C). This suggests, that α2I domain binds all of these ligands by the same mechanism, and that 229ox inhibits the binding either by interacting directly with the ligand recognition site or altering the three dimensional structure of the I domain to inactive one.

Figure 5:
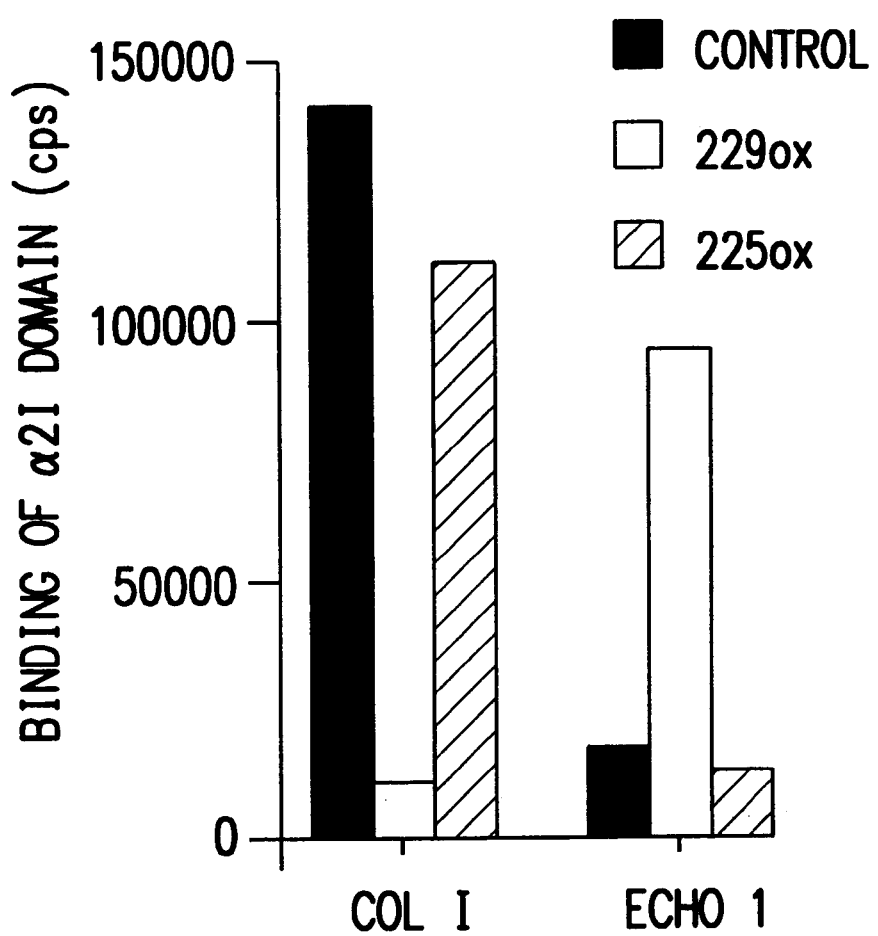
FIG. 5. The effect of 229ox on the binding of rα2I to type I collagen and echovirus-1. Microtiter plate wells were precoated with type I collagen and echovirus-1, rα2I was allowed to bind in the presence or absence of peptide. The data represent the mean from three parallel experiments.

Example 4
The Jararhagin-derived Peptide Activates the Echovirus-1 Recognition Site in Integrin rα1I Domain In addition to mediating cell adhesion to collagen and laminin- 1 integrin α2β1 also functions as a virus receptor, mediating cell surface attachment and infection by a human pathogen, echovirus-1. Matrix proteins and echovirus-1 have been found to interact with the integrin in an different manner, but the binding sites for echovirus-1 is also located in the I domain of α2 subunit. As described above rα2I domain showed weak binding to the coated echovirus-1, but surprisingly the addition of 229ox peptide increased this binding about 10-fold, when the control peptide 225ox had no effect (FIG. 5). This result indicates, that binding of the 229ox peptide to the α2I domain induces a structural change in the protein, which increases the binding affinity of rα2I to echovirus-1.

This suggests a possible activity modulation site on the I domain where the binding of RKK could allosterically inhibit binding to collagen. The RKK-induced change in the conformation of rα2I domain was evident in our experiments, where the RKK peptide did not only block rα2I domain adhesion to collagen, but also increased remarkably rα2I domain attachment to echovirus-1. In addition to confirming the previous suggestion, that echovirus-1 and collagen recognize distinct sites of α2I domain, the data indicate the existence of an important regulation mechanism of one ligand recognition site (echovirus-1 binding site) by the occupancy of another binding site (RKK-binding site). However, the existing information about α2I domain structure-function relationship is not sufficient for conclusion, whether RKK binds directly to the collagen recognition site or whether it is an allosteric inhibitor of α2I domain-collagen interaction. In both cases RKK containing peptides are very valuable tools for studies aimed to reveal the ligand recognition function of integrin I domains.

Figure 6A:
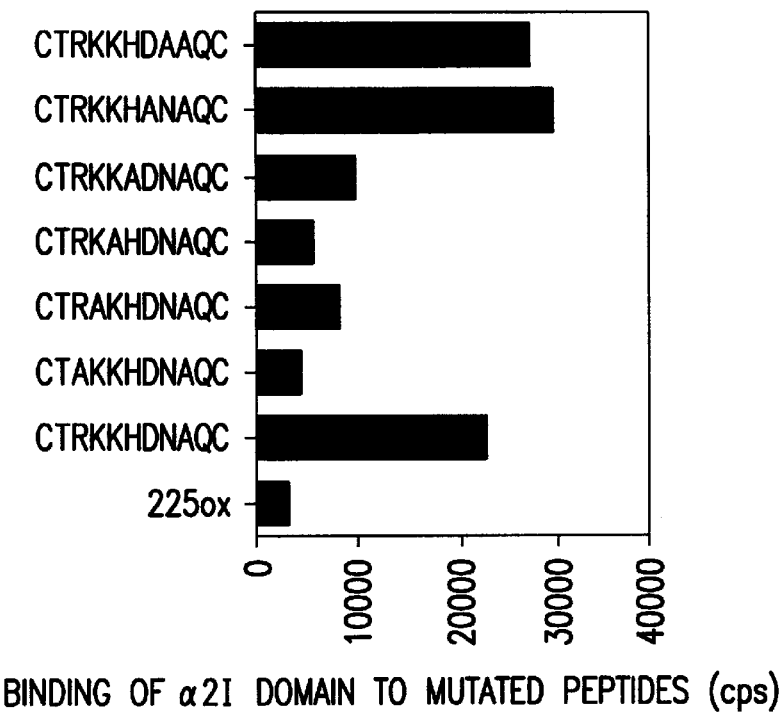
FIGS. 6(A–B). Inhibition of the binding of rα2I to type I collagen by alanine substituted 229ox peptides. The peptides were precoated to microtiter plate wells and rα2I was allowed to bind (A). Alternatively microtiter plate wells were precoated with type I collagen and rα2I was added in the presence of peptide (B).
Figure 6B:
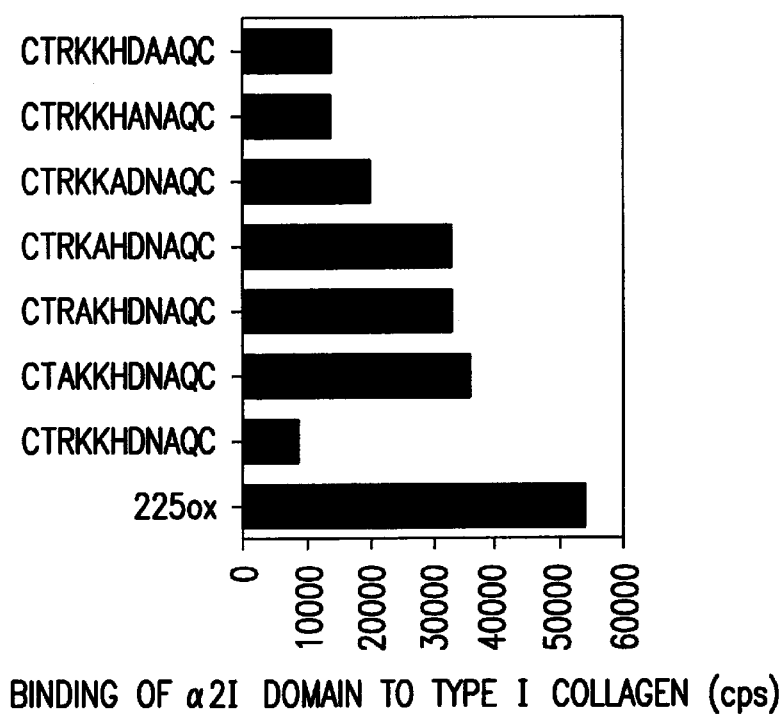

Example 5
The Sequence of Three Amino Acids, RKK, is Essential for binding to Integrin rα2I Domain The previously published information about integrin recognition sites in various proteins emphasizes the importance of two amino acid residues, namely aspartic acid and arginine. To reveal the critical amino acid residues inside the 229ox peptide, a series of new peptides were tested where amino acids in p229 were replaced one by one with alanine residues. The peptides were bound to solid phase and tested for their ability to bind rα2I. Interestingly three amino acids arginine-lysine-lysine (RKK) were found to be essential and the adjacent histidine showed some effect. The substitution of the aspartic acid or the asparagine residues had no effect (FIG. 6A). Consistent with this, rα2I binding to type I collagen was poorly inhibited with the peptides containing alanine substitutions of the RKK sequence, while substitution of the aspartic acid or the asparagine residues did not impair this function (FIG. 6B).

Figure 7A:
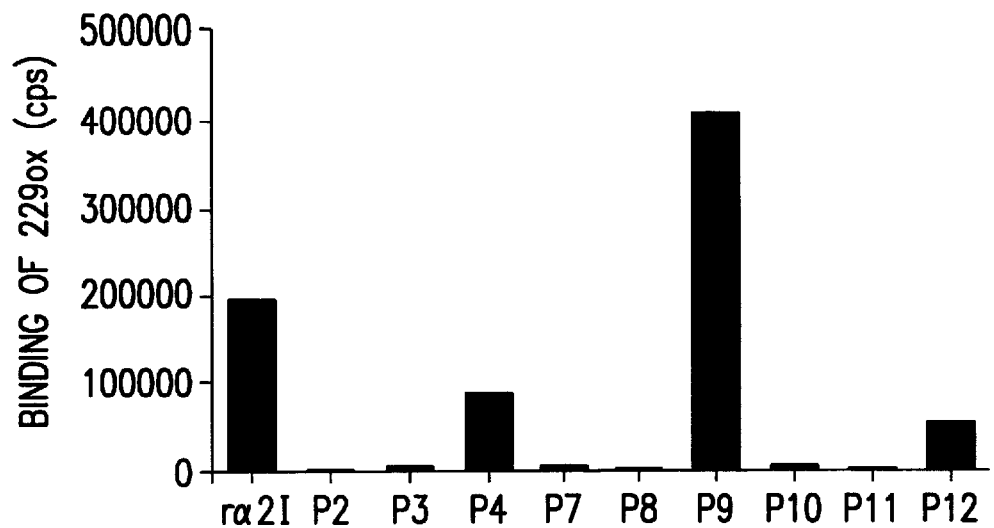
FIGS. 7(A–C). The α2I domain peptides (A) and rα2I (A,B) were bound to solid phase and biotinylated 229ox was added. Binding of 229ox peptide to α2I domain derived peptides is shown in (A). The importance of $Mg^{++}$ for the 229ox binding to solid phase bound rα2I is shown in (B). The importance of $Mg^{++}$ for the binding of rα2I to solid phase bound type I collagen and 229ox peptide is shown in (C).
Figure 7B:
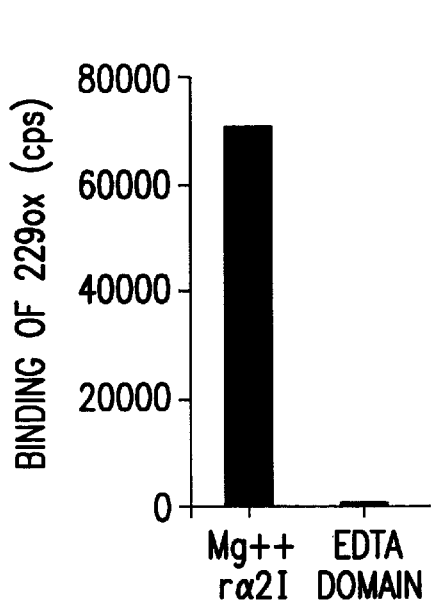
Figure 7C:
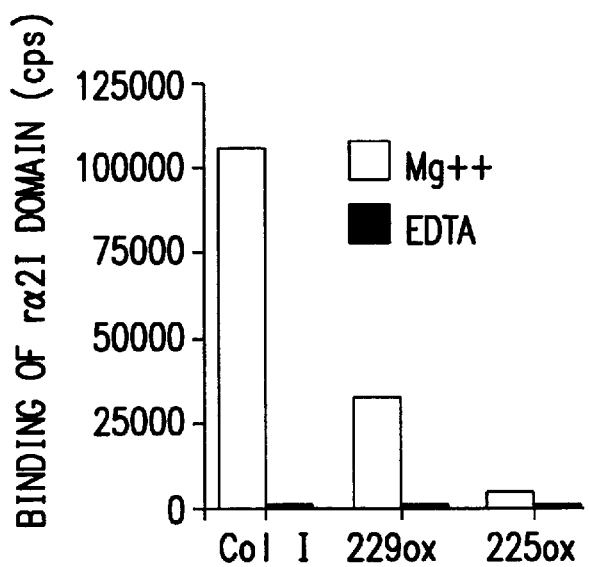

To identify possible binding sites in α2I for 229ox peptide a series of peptides corresponding to hydrophilic regions in the α2I domain was synthesized and tested for their ability to bind to biotinylated 229ox. The α2I domain peptides and rα2I were bound to solid phase and biotinylated 229ox was added. 229ox was shown to bind rα2I and peptide P9 significantly, while in repeated experiments there was no binding to other peptides (FIG. 7A). The interaction between biotinylated 229ox and solid phase bound rα2I was dependent on divalent cations (FIG. 7B) as was the binding of europium labeled rα2I to solid phase bound type I collagen and 229ox peptide (FIG. 7C).

Example 6
The Critical Length of the RKK-peptide

Figure 8:
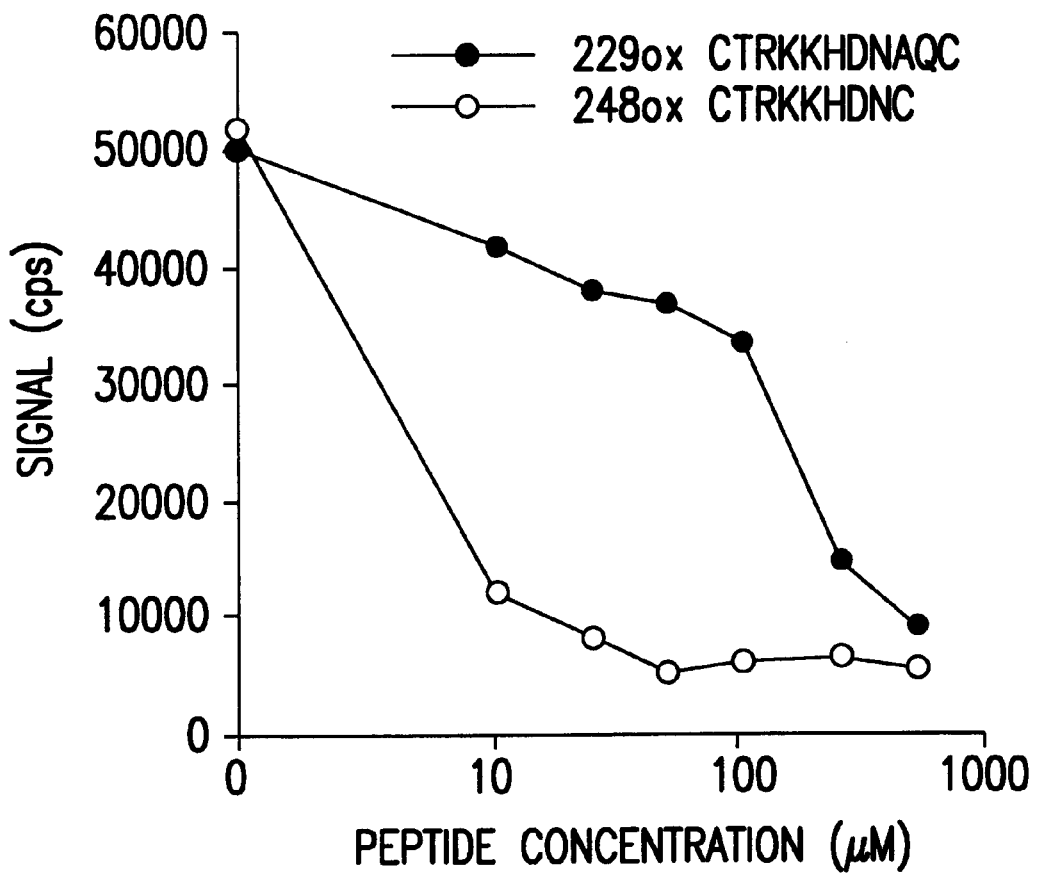
FIG. 8 Inhibition of the binding of recombinant α2I to collagen. The solid circles show the effect of the indicated concentrations of 229ox (CTRKKHDNAQC; SEQ ID No. 5). The open circles show the effect of 248ox (CTRKKHDNC; SEQ ID No. 4).

In order to determine the critical length of the RKK-peptide, a set of peptides were prepared comprising the RKK sequence and additional amino acids, as follows. CTRKKHDNAQC (229ox; SEQ ID No. 5), CTRKKHD-NAC (SEQ ID No. 34) and CTRKKHDNC (248ox; SEQ ID No. 4) were tested. The shortest peptide showed maximal inhibition of rα2I domain binding to collagen at a concentration of 10 μM. This was more than 10-fold more effective than the longer peptide 229ox (FIG. 8).

Example 7
Cell Migration Assays

A migration assay mimics the movement of cells in collagenous matrix This example demonstrates that the present peptides block movement of such cells and therefore are useful in therapeutic methods for treating diseases characterized by such cell migration.

To show the effects of 229ox/RKK-peptide and of 225 ox on cell-collagen interaction, chemically transformed HOS-MNNG cells were allowed to attach to type I collagen and then to migrate on it. The importance of α2β1 integrin in this process has been previously shown (Vihinen, P. et al., *Cell Growth Diff* 7:439–447 (1996)).

The cell migration assays were carried out as described previously (Vihinen, P. et al., *Cell Growth Diff.* 7:439–447 (1996)). Essentially, human HOS-MNNG osteosarcoma cells (ATCC) were suspended in serum-free Optimem 1 medium (Life Technologies, Inc.) and 20,000–30,000 cells/ well were transferred to a 24-well cell culture cluster (Costar) inside a metal cylinder having a diameter of 2.80 mm. The cell culture wells had been coated with 5 μg/cm$^2$ type I collagen. The cells were allowed to attach to collagen for 16 h at +37° C. The cylinders were removed, nonadherent cells were washed away with Optimem (Life Technologies, Inc) and the adherent cells were allowed to migrate in Optimem in the presence of peptides for 4 days. Fresh Optimem containing peptides was changed daily to the wells. After 4 days the surface area covered by the cells was measured with Microcomputer Imaging Device version M4 (Imaging Research Inc.).

Figure 9A:
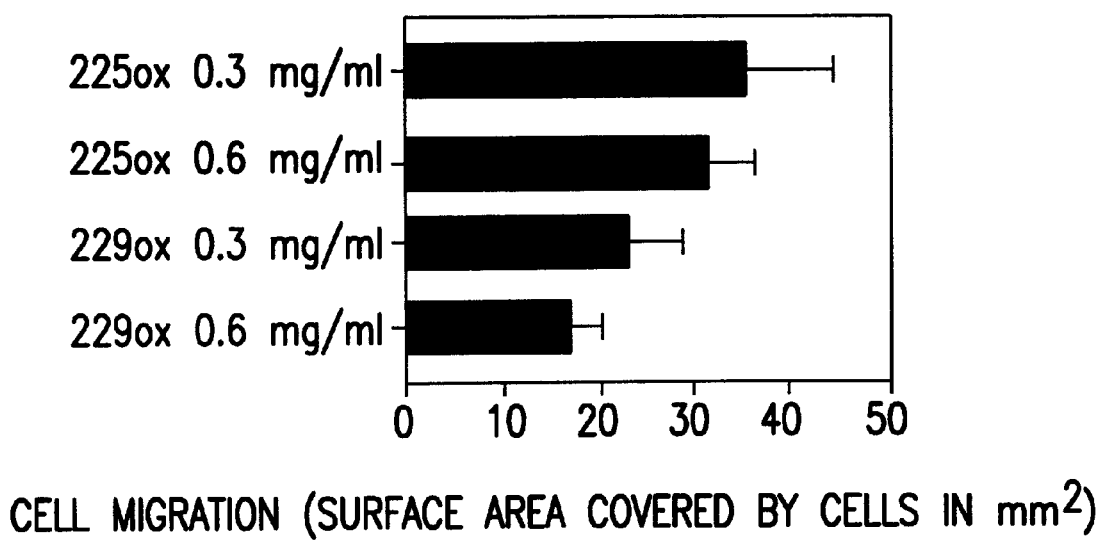
FIG. 9(A–B). Migration of HOS-MNNG cells on type I collagen. The cells were allowed to attach to the substrata. After 4 days the cells were stained, surface area covered by cells was determined by an image analyser (A) and wells were photographed (13).
Figure 9B:

The results of this experiment is shown in FIG. 9. Either 229ox or 225ox peptide was added to the cells at the concentration of 500 μM and fresh peptide was added daily. The ability of HOS-MNNG cells to migrate on type I collagen was not affected by 225ox control peptide, but 229ox peptide inhibited significantly (p<0.001, Student's t-test) the migration (FIG. 9).

This inhibition of osteosarcoma cell migration on collagen suggests that i) movement of malignant cells and, therefore, cancer cell invasion can be prevented by p229ox, and (ii) that migration of any cell type can also be inhibited when the migration is as a result of, at least in part, to α2β1 integrin-collagen interaction.

Example 8
Inhibition of Cell Adhesion by an RKK Peptide

Cell adhesion of human keratinocyte HaCaT cells and cell line UT-SCC-2 established from squamous cellular carcinoma of the mouth to type I collagen in the presence of peptide 220ox or a functional antibody against α2 integrin, Gi9 (an anti-alphα2-integrin antibody that is commercially available from Immunotech/Coulter, Westrbrook, Ma., USA). Cells were treated with cycloheximide 10 μg/ml in serum free medium for 1 h. The were detached and allowed to adhere to microtiter plates precoated with type I collagen for 1 h in DMEM with 0.1% glycine. Nonadherent cells were washed out and the adherent cells were stained with crystal violet and the number of adherent cells was estimated by measuring optical absorbance.

Figure 10:
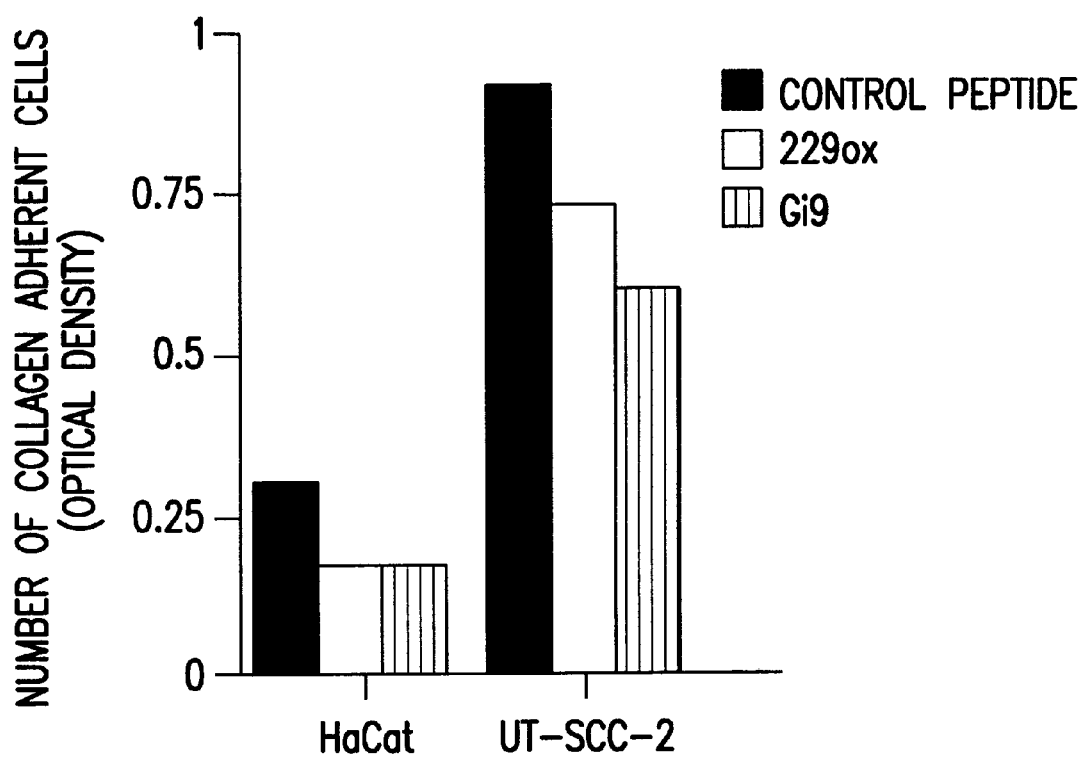
FIG. 10. Cell adhesion of HaCaT and UT-SCC-2 cells in the presence of 229ox and Gi9 antibody against α2 integrin.

The results summarized in FIG. 10 show that peptides according to the present invention, for example, peptide 229ox (p229ox) will inhibit cell migration and are therefore are useful in the treatment or prevention of disease conditions involving epithelial cell migration, such as, for example, periodontitis, as epithelial cells bind α2β1 integrin and use this binding to migrate along collagen.

Example 9
Use of an RKK Peptide in the Treatment of Periodontitis and Gingivitis Periodontitis is a disease characterized by inflammation and loss of tooth supportive connective tissue. The disease is initiated by pathogenic oral bacteria, which activate the tissue cells to produce and release hydrolytic enzymes that degrade tissue components. An essential feature of the disease process is increased proliferation and migration of epithelial cells that attach gingiva to the tooth surface functional epithelium/pocket epithelium).

Conventional treatment of periodontitis and gingivitis has focused on the removal of the pathogenic bacteria from the periodontium, either by mechanical scaling or by antibiotic treatment. Furthermore, surgical correction of the periodontal tissue architecture is frequently used.

The cell migration inhibition provided by the peptides of the invention, for example, p229ox, can be used alone or as an adjunct to other treatments to prevent or treat periodontal disease, including periodontitis and gingivitis. Specifically, compositions containing efficacious amounts of one or more of the circular peptides of the invention that contain the RKK sequence can be administered topically to a patient in need of treatment for periodontal disease, including periodontitis and gingivitis. A composition useful in this regard can be formulated for topical application using any conventional technique. The peptides of the invention can be formulated into carriers, including polymeric carriers such as, for example, those based upon ethyl cellulose, silicone rubbers, and especially degradable polymers and copolymers such as poly(lactic acid), poly(glycolic acid), poly (lactic acid)-poly(glycolic acid) copolymer, polyamides and polyesters, gelatin, collagen, albumin, and fibrinogen, cross-linked is desired to impart the desired RKK activity or release characteristics. Such delivery systems for the oral cavity are described, for examples, in U.S. Pat. No. 5,002, 769, U.S. Pat. No. 5,023,082, U.S. Pat. No. 5,160,737, U.S. Pat. No. 5,330,746, U.S. Pat. No. 5,425,953, U.S. Pat. No. 5,438,076 and U.S. Pat. No. 5,639,795, each incorporated herein by reference. The peptide is provided to the desired site in the oral cavity in an implant form, or as part of a liquid composition that solidifies in place in the oral cavity, or in the form of a toothpaste or gel that provides efficacious levels of the RKK-containing peptide to the desired site. The amount of the peptide of the invention is varied as desired so as to provide levels efficacious at providing the desired inhibitory effect in the environment of the oral cavity and the delivery system, but generally can be present at from about 0.001%–95% of the composition liquid composition prior to solidification or in the solid composition, depending upon the severity of the condition being treated.

A membrane can also be used as a support for providing the peptide of the invention to the desired site.

The RKK-containing peptides according to the invention are useful for the treatment and/or prophylaxis of diseases characterized by epithelial cell migration, especially for the treatment of medical conditions where topical applications are preferred.

Having now fully described this invention, it will be apparent to one of ordinary skill in the art that the same can be carried out with minor modifications that do not affect the content or spirit thereof

What is claimed is:

1. A peptide comprising an amino acid sequence CTRKKHDNC (SEQ ID NO. 4), wherein said peptide is cyclic.

2. A peptide comprising an amino acid sequence CTRKKHDNAQC (SEQ ID NO. 5), wherein said peptide is cyclic.

3. A peptide consisting of an amino acid sequence $X_1$RKKH$X_2X_n$ (SEQ ID NO:35), wherein $X_1$, $X_2$ and $X_n$ are any amino acid and n=1–4, and wherein said peptide is cyclic.

4. A peptide consisting of an amino acid sequence CTRKKHDNC (SEQ ID NO. 4), wherein said peptide is cyclic.

5. A peptide consisting of an amino acid sequence CTRKKHDNAQC (SEQ ID NO. 5), wherein said peptide is cyclic.

6. The peptide of claim 3, wherein n=3.

7. A peptide comprising an amino acid sequence C$X_1$RKKH$X_2X_n$ (SEQ ID NO:36), wherein $X_1$, $X_2$ and $X_n$ are any amino acids and n=1–4, and wherein said peptide is cyclic.

8. A peptide comprising an amino acid sequence $X_1$RKKH$X_2X_n$C (SEQ ID NO:37), wherein $X_1$, $X_2$ and $X_n$ are any amino acid and n=1–4, and wherein said peptide is cyclic.

9. A peptide comprising an amino acid sequence C$X_1$RKKH$X_2X_n$C (SEQ ID NO:38), wherein $X_1$, $X_2$ and $X_n$ are any amino acid and n=1–4, and wherein said peptide is cyclic.

10. A peptide comprising an amino acid sequence CTRKKHD (SEQ ID NO:5), wherein said peptide is cyclic.

11. A peptide comprising an amino acid sequence CTRKKHDNA (SEQ ID NO:7), wherein said peptide is cyclic.

12. A pharmaceutical composition comprising a peptide that comprises an amino acid sequence RKKH (SEQ ID NO. 8), and a pharmaceutically acceptable carrier, wherein said peptide is cyclic and said composition is suitable for topical administration.

13. A method for inhibiting an integrin containing the α2I domain from binding to molecules that recognize said α2I domain, said method comprising exposing said integrin to a peptide comprising an amino acid sequence RKKH (SEQ ID NO. 8), wherein said peptide is cyclic.

14. A method for inhibiting integrin-dependent cell migration in a patient, said method comprising providing a peptide comprising an amino acid sequence RKKH (SEQ ID NO. 8) to said patient in an amount that is efficacious to inhibit said integrin-dependent cell migration, wherein said peptide is cyclic.

15. The method of claim 14, wherein said cell migration is associated with cancer, cardiovascular disease or a periodontitis condition in said patient.

16. A method for inhibiting migration of cells attached to a collagen matrix in a patient in need of the same, said method comprising administering a peptide comprising an amino acid sequence RKKH (SEQ ID NO. 8) to said patient in an amount that is efficacious to inhibit said migration of cells attached to a collagen matrix, wherein said peptide is cyclic.

17. A method for inhibiting adhesion of platelets to collagen or collagen-induced platelet aggregation in a patient, said method comprising providing a peptide comprising an amino acid sequence RKKH (SEQ ID NO. 8) to said patient in an amount that is efficacious to inhibit said adhesion of platelets to collagen or said collagen-induced platelet aggregation, wherein said peptide is cyclic.

18. The method of claim 17, wherein said adhesion or aggregation is associated with cardiovascular disease in said patient.

19. A pharmaceutical composition comprising a peptide comprising an amino acid sequence $X_1$RKKH$X_2X_n$ (SEQ ID NO:35), and a pharmaceutically acceptable carrier, wherein $X_1$, $X_2$ and $X_n$ are any amino acid and n=1–4, and wherein said peptide is cyclic and said composition is suitable for topical administration.

20. A method for inhibiting an integrin containing the α2I domain from binding to molecules that recognize said α2I domain, said method comprising exposing said integrin to a peptide comprising an amino acid sequence $X_1RKKHX_2X_n$ (SEQ ID NO:35), wherein $X_1$, $X_2$ and $X_n$ are any amino acid and n=1–4, and wherein said peptide is cyclic.

21. A method for inhibiting integrin-dependent cell migration in a patient, said method comprising providing a peptide comprising an amino acid sequence $X_1RKKHX_2X_n$ (SEQ ID NO:35) to said patient in an amount that is efficacious to inhibit said integrin-dependent cell migration, wherein $X_1$, $X_2$ and $X_n$ are any amino acid and n=1–4, and wherein said peptide is cyclic.

22. The method of claim 21, wherein said cell migration is associated with cancer, cardiovascular disease or a periodontitis condition in said patient.

23. A method for inhibiting migration of cells attached to a collagen matrix in a patient in need of the same, said method comprising administering a peptide comprising an amino acid sequence $X_1RKKHX_2X_n$ (SEQ ID NO:35) to said patient in an amount that is efficacious to inhibit said migration of cells attached to a collagen matrix, wherein $X_1$, $X_2$ and $X_n$ are any amino acid and n=1–4, and wherein said peptide is cyclic.

24. A method for inhibiting adhesion of platelets to collagen or collagen-induced platelet aggregation in a patient, said method comprising providing a peptide comprising an amino acid sequence $X_1RKKHX_2X_n$ (SEQ ID NO:35) to said patient in an amount that is efficacious to inhibit said adhesion of platelets to collagen or said collagen-induced platelet aggregation, wherein $X_1$, $X_2$ and $X_n$ are any amino acid and n=1–4, and wherein said peptide is cyclic.

25. The method of claim 24, wherein said adhesion or aggregation is associated with cardiovascular disease in said patient.

26. A fragment of a peptide, wherein said peptide consists of the amino acid sequence $X_1RKKHX_2X_n$ (SEQ ID NO:35), wherein $X_1$, $X_2$ and $X_n$ are any amino acid and n=1–4, wherein said fragment lacks one or more of the amino acids $X_1$, $X_2$ and $X_n$, and wherein said fragment is cyclic.

27. A fragment of a peptide, wherein said peptide consists of the amino acid sequence CTRKKHDNC (SEQ ID NO. 4), wherein said fragment lacks one or more of amino acids C, T, H, D, N, A or Q, and wherein said fragment is cyclic.

28. A fragment of a peptide, wherein said peptide consists of the amino acid sequence CTRKKHDNAQC (SEQ ID NO. 5), wherein said fragment lacks one or more of amino acids C, T, H, D, N, A or Q, and wherein said fragment is cyclic.

29. A pharmaceutical composition, comprising the peptide of any one of claims 1–11 and 26, and a pharmaceutically acceptable carrier.

30. The pharmaceutical composition according to claim 29, wherein the composition is suitable for topical administration.

31. A method for inhibiting an integrin containing the α2I domain from binding to molecules that recognize said α2I domain, said method comprising exposing said integrin to said peptide of any one of claims 1–11 and 26.

32. A method for inhibiting integrin-dependent cell migration in a patient, said method comprising providing said peptide of any one of claims 1–11 and 26 to said patient in an amount that is efficacious to inhibit said integrin-dependent cell migration.

33. The method of claim 32, wherein said cell migration is associated with cancer, cardiovascular disease or a periodontitis condition in said patient.

34. A method for inhibiting migration of cells attached to a collagen matrix in a patient in need of the same, said method comprising administering said peptide of any one of claims 1–11 and 26 to said patient in an amount that is efficacious to inhibit said migration of cells.

35. A method for inhibiting adhesion of platelets to collagen or collagen-induced platelet aggregation in a patient, said method comprising providing said peptide of any one of claims 1–11 and 26 to said patient in an amount at is efficacious to inhibit said adhesion of platelets to collagen or said collagen-induced platelet aggregation.

36. The method of claim 35, wherein said adhesion or aggregation are associated with cardiovascular disease in said patient.

37. The peptide of any one of claims 1–11 and 26, wherein said peptide is cyclic due to covalent bonding.

38. The peptide of any one of claims 1–11 and 26 which binds to integrin.

39. The peptide of claim 38, wherein said integrin is α2β1.

40. The peptide of claim 37, wherein said peptide is cyclic due to disulfide bonding between two cysteine residues.

* * * * *

```
                         SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
         (A) LENGTH: 9 amino acids
         (B) TYPE: amino acid
         (D) TOPOLOGY: circular (ii) MOLECULE TYPE: peptide (xi) SEQUENCE DESCRIPTION: SEQ ID NO:1:

Xaa Arg Lys Lys Xaa Xaa Xaa Xaa Xaa
1               5

(2) INFORMATION FOR SEQ ID NO:2:

(i) SEQUENCE CHARACTERISTICS:
         (A) LENGTH: 8 amino acids
         (B) TYPE: amino acid
         (D) TOPOLOGY: circular (ii) MOLECULE TYPE: peptide (xi) SEQUENCE DESCRIPTION: SEQ ID NO:2:

Xaa Arg Lys Lys Xaa Xaa Xaa Xaa
1               5

(2) INFORMATION FOR SEQ ID NO:3:

(i) SEQUENCE CHARACTERISTICS:
         (A) LENGTH: 7 amino acids
         (B) TYPE: amino acid
         (D) TOPOLOGY: circular (ii) MOLECULE TYPE: peptide (xi) SEQUENCE DESCRIPTION: SEQ ID NO:3:

Xaa Arg Lys Lys Xaa Xaa Xaa
1               5

(2) INFORMATION FOR SEQ ID NO:4:

(i) SEQUENCE CHARACTERISTICS:
         (A) LENGTH: 9 amino acids
         (B) TYPE: amino acid
         (D) TOPOLOGY: circular (ii) MOLECULE TYPE: peptide
```

(xi) SEQUENCE DESCRIPTION: SEQ ID NO:4:

Cys Thr Arg Lys Lys His Asp Asn Cys
1               5

(2) INFORMATION FOR SEQ ID NO:5:

(i) SEQUENCE CHARACTERISTICS:
        (A) LENGTH: 11 amino acids
        (B) TYPE: amino acid
        (D) TOPOLOGY: circular (ii) MOLECULE TYPE: peptide (xi) SEQUENCE DESCRIPTION: SEQ ID NO:5:

Cys Thr Arg Lys Lys His Asp Asn Ala Gln Cys
1               5                   10

(2) INFORMATION FOR SEQ ID NO:6:

(i) SEQUENCE CHARACTERISTICS:
        (A) LENGTH: 7 amino acids
        (B) TYPE: amino acid
        (D) TOPOLOGY: circular (ii) MOLECULE TYPE: peptide (xi) SEQUENCE DESCRIPTION: SEQ ID NO:6:

Cys Thr Arg Lys Lys His Asp
1               5

(2) INFORMATION FOR SEQ ID NO:7:

(i) SEQUENCE CHARACTERISTICS:
        (A) LENGTH: 9 amino acids
        (B) TYPE: amino acid
        (D) TOPOLOGY: circular (ii) MOLECULE TYPE: peptide (xi) SEQUENCE DESCRIPTION: SEQ ID NO:7:

Cys Thr Arg Lys Lys His Asp Asn Ala
1               5

(2) INFORMATION FOR SEQ ID NO:8:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:8:

Arg Lys Lys His
1

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

CACAGGGATC CCCTGATTTT CAGCTC                                          26

(2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

GTGGCTGAAT TCAACAGTAC CTTCAATG                                          28

(2) INFORMATION FOR SEQ ID NO:11:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:11:

Pro Asp Phe Gln
1

(2) INFORMATION FOR SEQ ID NO:12:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:12:

Ile Glu Gly Thr Val
1           5

(2) INFORMATION FOR SEQ ID NO:13:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:13:

Glu Phe Ile Val Thr Asp
1           5

(2) INFORMATION FOR SEQ ID NO:14:

(i) SEQUENCE CHARACTERISTICS:
        (A) LENGTH: 10 amino acids
        (B) TYPE: amino acid
        (D) TOPOLOGY: circular (ii) MOLECULE TYPE: peptide (xi) SEQUENCE DESCRIPTION: SEQ ID NO:14:

Cys Trp Ser Asn Gly Asp Lys Ile Thr Cys
1           5                 10

(2) INFORMATION FOR SEQ ID NO:15:

(i) SEQUENCE CHARACTERISTICS:
            (A) LENGTH: 11 amino acids
            (B) TYPE: amino acid
            (D) TOPOLOGY: circular (ii) MOLECULE TYPE: peptide (xi) SEQUENCE DESCRIPTION: SEQ ID NO:15:

Cys Glu Gln Gln Arg Tyr Asp Pro Tyr Lys Cys
1               5                   10

(2) INFORMATION FOR SEQ ID NO:16:

(i) SEQUENCE CHARACTERISTICS:
            (A) LENGTH: 11 amino acids
            (B) TYPE: amino acid
            (D) TOPOLOGY: circular (ii) MOLECULE TYPE: peptide (xi) SEQUENCE DESCRIPTION: SEQ ID NO:16:

Cys Lys Leu Pro Asp Ser Glu Ala His Ala Cys
1               5                   10

(2) INFORMATION FOR SEQ ID NO:17:

(i) SEQUENCE CHARACTERISTICS:
            (A) LENGTH: 11 amino acids
            (B) TYPE: amino acid
            (D) TOPOLOGY: circular (ii) MOLECULE TYPE: peptide (xi) SEQUENCE DESCRIPTION: SEQ ID NO:17:

Cys His Tyr Ser Pro Asp Gly Arg Glu Ile Cys
1               5                   10

(2) INFORMATION FOR SEQ ID NO:18:

(i) SEQUENCE CHARACTERISTICS:
            (A) LENGTH: 10 amino acids
            (B) TYPE: amino acid
            (D) TOPOLOGY: circular (ii) MOLECULE TYPE: peptide (xi) SEQUENCE DESCRIPTION: SEQ ID NO:18:

Cys Pro Ala Asp Val Phe His Lys Asn Cys
1               5                   10

(2) INFORMATION FOR SEQ ID NO:19:

(i) SEQUENCE CHARACTERISTICS:
            (A) LENGTH: 11 amino acids
            (B) TYPE: amino acid
            (D) TOPOLOGY: circular (ii) MOLECULE TYPE: peptide (xi) SEQUENCE DESCRIPTION: SEQ ID NO:19:

Cys Tyr Ser Asn Asp Asp Glu His Lys Gly Cys
1               5                   10

(2) INFORMATION FOR SEQ ID NO:20:

(i) SEQUENCE CHARACTERISTICS:
            (A) LENGTH: 10 amino acids
            (B) TYPE: amino acid
            (D) TOPOLOGY: circular (ii) MOLECULE TYPE: peptide (xi) SEQUENCE DESCRIPTION: SEQ ID NO:20:

Val Cys Asp Glu Ser Asn Ser Ile Tyr Cys
1               5                   10

(2) INFORMATION FOR SEQ ID NO:21:

(i) SEQUENCE CHARACTERISTICS:
           (A) LENGTH: 17 amino acids
           (B) TYPE: amino acid
           (D) TOPOLOGY: circular (ii) MOLECULE TYPE: peptide (xi) SEQUENCE DESCRIPTION: SEQ ID NO:21:

Val Cys Asp Glu Ser Asn Ser Ile Tyr Pro Trp Asp Ala Val Lys Asn Cys
1               5                   10                  15

(2) INFORMATION FOR SEQ ID NO:22:

(i) SEQUENCE CHARACTERISTICS:
           (A) LENGTH: 17 amino acids
           (B) TYPE: amino acid
           (D) TOPOLOGY: linear (ii) MOLECULE TYPE: peptide (xi) SEQUENCE DESCRIPTION: SEQ ID NO:22:

Ile Tyr Pro Trp Asp Ala Val Lys Asn Phe Leu Glu Lys Phe Val Gln Gly
1               5                   10                  15

(2) INFORMATION FOR SEQ ID NO:23:

(i) SEQUENCE CHARACTERISTICS:
           (A) LENGTH: 16 amino acids
           (B) TYPE: amino acid
           (D) TOPOLOGY: linear (ii) MOLECULE TYPE: peptide (xi) SEQUENCE DESCRIPTION: SEQ ID NO:23:

Ala Val Lys Asn Phe Leu Glu Lys Phe Val Gln Gly Leu Asp Ile Gly
1               5                   10                  15

(2) INFORMATION FOR SEQ ID NO:24:

(i) SEQUENCE CHARACTERISTICS:
           (A) LENGTH: 16 amino acids
           (B) TYPE: amino acid
           (D) TOPOLOGY: linear (ii) MOLECULE TYPE: peptide (xi) SEQUENCE DESCRIPTION: SEQ ID NO:24:

Leu Asp Ile Gly Pro Thr Lys Thr Gln Val Gly Lys Ile Gln Tyr Ala
1               5                   10                  15

(2) INFORMATION FOR SEQ ID NO:25:

(i) SEQUENCE CHARACTERISTICS:
           (A) LENGTH: 20 amino acids
           (B) TYPE: amino acid
           (D) TOPOLOGY: linear (ii) MOLECULE TYPE: peptide (xi) SEQUENCE DESCRIPTION: SEQ ID NO:25:

```
Gln Tyr Ala Asn Asn Pro Arg Val Val Phe Asn Leu Asn Thr Tyr Lys Thr
 1               5                  10                  15

Lys Glu Glu
        20
```

(2) INFORMATION FOR SEQ ID NO:26:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:26:

```
Leu Asn Thr Tyr Lys Thr Lys Glu Glu Met Ile Val Ala Thr
 1               5                  10
```

(2) INFORMATION FOR SEQ ID NO:27:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:27:

```
Ala Thr Ser Gln Thr Ser Gln Tyr Gly Gly Asp Lys Thr Asn Thr
 1               5                  10                  15
```

(2) INFORMATION FOR SEQ ID NO:28:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:28:

```
Arg Lys Tyr Ala Tyr Ser Ala Ala Ser Gly Gly Arg Arg Ser Ala Thr
 1               5                  10                  15
```

(2) INFORMATION FOR SEQ ID NO:29:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:29:

```
Thr Asp Gly Glu Ser His Asp Gly Ser Met Leu Lys Ala Val Ile Asp Gln
 1               5                  10                  15
```

(2) INFORMATION FOR SEQ ID NO:30:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:30:

```
Leu Asp Thr Lys Asn Leu Ile Lys Glu Ile Lys Ala Ile Ala Ser Ile Pro
 1               5                  10                  15

Thr Glu Arg
        20

(2) INFORMATION FOR SEQ ID NO:31:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:31:

Ser Asp Glu Ala Ala Leu Leu Glu Lys Ala Gly Thr Leu Gly Glu Gln
 1               5                  10                  15

(2) INFORMATION FOR SEQ ID NO:32:

(i) SEQUENCE CHARACTERISTICS:
        (A) LENGTH: 10 amino acids
        (B) TYPE: amino acid
        (D) TOPOLOGY: circular (ii) MOLECULE TYPE: peptide (xi) SEQUENCE DESCRIPTION: SEQ ID NO:32:

Gly Ala Cys Arg Gly Asp Cys Leu Gly Ala
 1               5                  10

(2) INFORMATION FOR SEQ ID NO:33:

(i) SEQUENCE CHARACTERISTICS:
        (A) LENGTH: 10 amino acids
        (B) TYPE: amino acid
        (D) TOPOLOGY: circular (ii) MOLECULE TYPE: peptide (xi) SEQUENCE DESCRIPTION: SEQ ID NO:33:

Gly Ala Cys Arg Gly Glu Cys Leu Gly Ala
 1               5                  10

(2) INFORMATION FOR SEQ ID NO:34:

(i) SEQUENCE CHARACTERISTICS:
        (A) LENGTH: 10 amino acids
        (B) TYPE: amino acid
        (D) TOPOLOGY: circular (ii) MOLECULE TYPE: peptide (xi) SEQUENCE DESCRIPTION: SEQ ID NO:34:

Cys Thr Arg Lys Lys His Asp Gln Ala Cys
 1               5

(2) INFORMATION FOR SEQ ID NO:35:

(i) SEQUENCE CHARACTERISTICS:
        (A) LENGTH: 7 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION: 1
```

(D) OTHER INFORMATION: /note= "May be any amino acid"

(ix) FEATURE:
            (A) NAME/KEY: Modified-site
            (B) LOCATION: 6
            (D) OTHER INFORMATION: /note= "May be any amino acid"

(ix) FEATURE:
            (A) NAME/KEY: Modified-site
            (B) LOCATION: 7
            (D) OTHER INFORMATION: /note= "Xn. May be any amino acid
                where n=1-4"

(xi) SEQUENCE DESCRIPTION: SEQ ID NO:35:

Xaa Arg Lys Lys His Xaa Xaa
1               5

(2) INFORMATION FOR SEQ ID NO:36:

(i) SEQUENCE CHARACTERISTICS:
            (A) LENGTH: 8 amino acids
            (B) TYPE: amino acid
            (D) TOPOLOGY: circular (ii) MOLECULE TYPE: peptide (ix) FEATURE:
            (A) NAME/KEY: Modified-site
            (B) LOCATION: 2
            (D) OTHER INFORMATION: /note= "May be any amino acid"

(ix) FEATURE:
            (A) NAME/KEY: Modified-site
            (B) LOCATION: 7
            (D) OTHER INFORMATION: /note= "May be any amino acid"

(ix) FEATURE:
            (A) NAME/KEY: Modified-site
            (B) LOCATION: 8
            (D) OTHER INFORMATION: /note= "Xn.  May be any amino acid
                where n=1-4"

(xi) SEQUENCE DESCRIPTION: SEQ ID NO:36:

Cys Xaa Arg Lys Lys His Xaa Xaa
1               5

(2) INFORMATION FOR SEQ ID NO:37:

(i) SEQUENCE CHARACTERISTICS:
            (A) LENGTH: 8 amino acids
            (B) TYPE: amino acid
            (D) TOPOLOGY: circular (ii) MOLECULE TYPE: peptide (ix) FEATURE:
            (A) NAME/KEY: Modified-site
            (B) LOCATION: 1
            (D) OTHER INFORMATION: /note= "May be any amino acid"

(ix) FEATURE:
            (A) NAME/KEY: Modified-site
            (B) LOCATION: 6
            (D) OTHER INFORMATION: /note= "May be any amino acid"

(ix) FEATURE:
            (A) NAME/KEY: Modified-site
            (B) LOCATION: 7
            (D) OTHER INFORMATION: /note= "Xn. May be any amino acid
                where n=1-4"

(xi) SEQUENCE DESCRIPTION: SEQ ID NO:37:

Xaa Arg Lys Lys His Xaa Xaa Cys
1               5

(2) INFORMATION FOR SEQ ID NO:38:

(i) SEQUENCE CHARACTERISTICS:
        (A) LENGTH: 9 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION: 2
        (D) OTHER INFORMATION: /note= "May be any amino acid"

(ix) FEATURE:
        (A) NAME/KEY: Modified-site
        (B) LOCATION: 7
        (D) OTHER INFORMATION: /note= "May be any amino acid"

(ix) FEATURE:
        (A) NAME/KEY: Modified-site
        (B) LOCATION: 8
        (D) OTHER INFORMATION: /note= "Xn. May be any amino acid
            where n=1-4"

(xi) SEQUENCE DESCRIPTION: SEQ ID NO:38:

Cys Xaa Arg Lys Lys His Xaa Xaa Cys
1           5